(12) United States Patent
Kim et al.

(10) Patent No.: US 10,338,238 B2
(45) Date of Patent: Jul. 2, 2019

(54) X-RAY DETECTOR AND X-RAY IMAGING APPARATUS HAVING THE SAME

(71) Applicant: SAMSUNG ELECTRONICS CO., LTD., Suwon-si (KR)

(72) Inventors: Young Ik Kim, Suwon-si (KR); Jin-Woo Park, Osan-si (KR); Eun Jeong Jo, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 540 days.

(21) Appl. No.: 14/953,051

(22) Filed: Nov. 27, 2015

(65) Prior Publication Data

US 2016/0154125 A1 Jun. 2, 2016

Related U.S. Application Data

(60) Provisional application No. 62/085,362, filed on Nov. 28, 2014.

(30) Foreign Application Priority Data

| May 28, 2015 | (KR) | ........................ 10-2015-0075445 |
| Oct. 19, 2015 | (KR) | ........................ 10-2015-0145281 |
| Nov. 25, 2015 | (KR) | ........................ 10-2015-0165928 |

(51) Int. Cl.
*G01T 7/00* (2006.01)
*A61B 6/00* (2006.01)

(52) U.S. Cl.
CPC .............. *G01T 7/00* (2013.01); *A61B 6/4283* (2013.01); *A61B 6/44* (2013.01)

(58) Field of Classification Search
None
See application file for complete search history.

(56) References Cited

U.S. PATENT DOCUMENTS 6,557,705 B1 * 5/2003 Nakajo .................. G03B 42/04
206/455
2011/0248173 A1 10/2011 Ogura
(Continued)

FOREIGN PATENT DOCUMENTS

EP 2910189 A1 8/2015

OTHER PUBLICATIONS

Communication dated Apr. 19, 2016, issued by the European Patent Office in counterpart European Application No. 15196764.3.
(Continued)

*Primary Examiner* — Hoon K Song
(74) *Attorney, Agent, or Firm* — Sughrue Mion, PLLC

(57) ABSTRACT

Disclosed herein are an X-ray detector, in which an active area of the X-ray detector has an improved structure for a user's convenience, and an X-ray imaging apparatus having the same, The X-ray detector is configured to detect X-rays irradiated from an X-ray source, and includes: a top frame that includes a first area, a second area which is bent from the first area, and an active area which is biased from a center of the first area; a side frame that includes a top frame resting part which is formed in an outer surface which faces an outside of the X-ray detector and on which the second area rests, the side frame being coupled with the top frame to form an accommodation space; and a sensor panel disposed in the accommodation space and configured to convert the detected X-rays into an electrical signal, the sensor panel being biased from the center of the first area to correspond to the active area.

21 Claims, 26 Drawing Sheets

(56) References Cited

U.S. PATENT DOCUMENTS

2013/0043400 A1 2/2013 Nakatsugawa et al.
2014/0016757 A1* 1/2014 Tateishi .................... G01T 1/16
378/189

OTHER PUBLICATIONS

Communication dated Jun. 27, 2018, issued by the European Patent Office in counterpart European Application No. 15 196 764.3.

* cited by examiner (a)

(b)

(a)

(b)

(a)

(b)

(a)

(b)

X-RAY DETECTOR AND X-RAY IMAGING APPARATUS HAVING THE SAME

CROSS-REFERENCE TO RELATED APPLICATIONS

This application claims the benefit of U.S. Provisional Patent Application No. 62/085,362, filed on Nov. 28, 2014 in the U.S. Patent and Trademark Office, and priority from Korean Patent Application No. 10-2015-0075445, filed on May 28, 2015, Korean Patent Application No. 10-2015-0145281, filed on Oct. 19, 2015, and Korean Patent Application No. 10-2015-0165928, filed on Nov. 25, 2015 in the Korean Intellectual Property Office, the disclosures of which are incorporated herein by reference in their respective entireties.

BACKGROUND

1. Field

Exemplary embodiments relate to an X-ray detector and an X-ray imaging apparatus having the same, and more particularly, to an X-ray detector, in which an active area of the X-ray detector has an improved structure for a user's convenience, and an X-ray imaging apparatus having the same.

2. Description of the Related Art

An X-ray imaging apparatus is equipment that is used for acquiring images of the inside of an object by using X-rays. The X-ray imaging apparatus images the inside of an object by using a non-invasive method of irradiating X-rays onto the object and detecting X-rays that propagate through the object. Accordingly, a medical X-ray imaging apparatus is used to diagnose an internal injury or a disease of an object that cannot be examined externally.

The X-ray imaging apparatus includes an X-ray source configured to generate X-rays and to irradiate the X-rays onto an object, and an X-ray detector configured to detect X-rays that propagate through the object. In order to image various parts of an object, the X-ray source can be configured to be movable. The X-ray detector can be used in a table mode when the X-ray detector is installed in a radiography table, in a stand mode when the X-ray detector is installed in a radiography stand, and in a portable mode when the X-ray detector is not fixed at a specific location.

Generally, an active area of an X-ray detector is formed in the center of the X-ray detector. Accordingly, when an object is positioned at or near the edge of the X-ray detector, it is difficult to acquire images about the inside of the object. In particular, when radiography is performed on an animal, it is difficult to acquire satisfying X-ray images, because it is not easy to accurately position the animal in the center of an X-ray detector.

SUMMARY

Therefore, it is an aspect of the exemplary embodiments to provide an X-ray detector having an improved structure capable of expanding an active area of the X-ray detector, and an X-ray imaging apparatus having the same.

It is another aspect of the exemplary embodiments to provide an X-ray detector having a structure in which an active area of the X-ray detector is changed and an X-ray imaging apparatus having the same.

Additional aspects of the exemplary embodiments will be set forth in part in the description which follows and, in part, will be apparent from the description, or may be learned by practice of the exemplary embodiments.

In accordance with one aspect of one or more exemplary embodiments, there is provided an X-ray detector configured to detect X-rays irradiated from an X-ray source, the X-ray detector including: a top frame that includes a first area, a second area which is bent from the first area, and an active area which is biased from a center of the first area; a side frame that includes a top frame resting part which is formed in an outer surface which faces an outside of the X-ray detector and on which the second area rests, the side frame being coupled with the top frame to form an accommodation space; and a sensor panel disposed in the accommodation space and configured to convert the detected X-rays into an electrical signal, the sensor panel being biased from the center of the first area to correspond to the active area.

The first area may include: a first edge which meets the second area; and a plurality of second edges which define the first area together with the first edge, wherein the active area is formed in the first area so as to be biased toward the first edge from the center of the first area.

The active area may include: a first border area that corresponds to the first edge; and a plurality of second border areas which constitute the active area together with the first border area, wherein a distance between the first edge and the first border area may be smaller than each of respective distances between each of the plurality of second edges and each of the plurality of second border areas.

The side frame may include: a body which forms a first surface of the top frame resting part, and which is disposed behind the second area with respect to an inward direction of the X-ray detector; and an outer protrusion part which forms a second surface of the top frame resting part, and which protrudes from the body in an outward direction of the X-ray detector.

The body may extend in a thickness direction of the X-ray detector so as to be adjacent to an inner surface of the first area.

The side frame may further include an inner protrusion part which protrudes from the body in the inward direction of the X-ray detector.

The X-ray detector may further include a middle block disposed in the accommodation space, and configured to support the sensor panel, wherein a first edge of the middle block may be located between the inner protrusion part and the first area, with respect to the thickness direction of the X-ray detector, such that the first edge of the middle block is spaced from the inner protrusion part.

The X-ray detector may further include a middle block disposed in the accommodation space, and configured to support the sensor panel, wherein the middle block may be spaced from the body in order to prevent an external impact that is applied on the side frame from being transferred to the sensor panel.

The X-ray detector may further include a bottom frame which forms an outer appearance of the X-ray detector together with the top frame and the side frame, wherein a first edge of the bottom frame may rest on a bottom frame resting part formed by a first surface of the inner protrusion part and a first surface of the body which faces an inside of the X-ray detector.

The bottom frame may be fixed at the inner protrusion part by a fixing member that penetrates through the bottom frame in the thickness direction of the X-ray detector.

The second area may be fixed on the top frame resting part by an adhesive material located between the second area and the top frame resting part.

A plurality of openings may be formed in the body, and the second area may be coupled with the top frame resting part by an adhesive material which passes through at least one from among the plurality of openings from the accommodation space in the outward direction of the X-ray detector.

The second area may be fixed at the body by a coupling member that penetrates through the second area in the inward direction of the X-ray detector.

The body may extend in the inward direction of the X-ray detector.

The X-ray detector may further include a middle block disposed in the accommodation space, and configured to support the sensor panel, wherein the body may extend in a thickness direction of the X-ray detector, and is spaced from an inner surface of the first area by a distance that is equal to or greater than a sum of a first thickness that is a thickness of the sensor panel and a second thickness that is a thickness of the middle block, so that a first edge of the sensor panel and a first edge of the middle block are disposed between the inner surface of the first area and a first surface of the body that is opposite to the first area.

At least one from among the first edge of the sensing panel and the first edge of the middle block may be located behind the second area, with respect to the inward direction of the X-ray detector, so as to directly face an inner surface of the second area while being adjacent to the inner surface of the second area.

The middle block may include a rib that protrudes in the thickness direction of the X-ray detector so that the middle block is spaced from the active area, and the rib may limit a movement of the middle block by interfering with a first edge of the body which extends in the inward direction of the X-ray detector so that a second edge of the middle block is spaced by a predetermined distance from the inner surface of the second area.

A buffer member may be disposed between the rib and the first edge of the body.

The middle block may include a rib that protrudes in the thickness direction of the X-ray detector so that the middle block is spaced from the active area, and a height of the rib may be greater than a height of the body in the thickness direction of the X-ray detector.

In accordance with another aspect of one or more exemplary embodiments, an X-ray imaging apparatus includes: an X-ray source configured to generate X-rays, and to irradiate the generated X-rays; and an X-ray detector configured to detect the irradiated X-rays, wherein the X-ray detector includes: a top frame that includes a first area, a second area which is bent from the first area, and an active area which is formed in the first area; a side frame that includes a top frame resting part which is formed in an outer surface which faces an outside of the X-ray detector and on which the second area rests, the side frame being coupled with the top frame to form an accommodation space; and a sensor panel configured to convert the detected X-rays into an electrical signal, wherein the accommodation space includes: a first accommodation subspace; and a second accommodation subspace which has a greater width than the first accommodation subspace in a width direction of the X-ray detector, and in which the sensor panel expands in an outward direction of the X-ray detector, and wherein the active area may expand in an outward direction of the first area to correspond to the sensor panel.

The second accommodation subspace may be formed adjacent to the first area in a thickness direction of the X-ray detector.

The side frame may include a body which forms a first surface of the top frame resting part, and which is disposed behind the second area with respect to an inward direction of the X-ray detector.

The body may extend in a thickness direction of the X-ray detector so as to face at least a first part of an inner surface of the second area.

The side frame may further include an inner protrusion part that protrudes from the body in the inward direction of the X-ray detector so as to form the first accommodation subspace.

The X-ray detector may further include a middle block disposed in the second accommodation subspace, and configured to support the sensor panel, wherein a first edge of the middle block may be located between the inner protrusion part and the first area in a thickness direction of the X-ray detector such that the first edge of the middle block is spaced from the inner protrusion part.

The X-ray detector may further include a middle block disposed in the second accommodation subspace, and configured to support the sensor panel, wherein a first edge of the middle block may be located adjacent to an inner surface of the body in a width direction of the X-ray detector.

The body may extend in the inward direction of the X-ray detector to form the first accommodation subspace.

The X-ray detector may further include a middle block disposed in the second accommodation subspace, and configured to support the sensor panel, wherein at least one from among a first edge of the sensing panel and a first edge of the middle block may be located behind the second area, with respect to the inward direction of the X-ray detector, so as to directly face an inner surface of the second area while being adjacent to the inner surface of the second area.

The side frame may further include an outer protrusion part which forms a second surface of the top frame resting part, and which protrudes from the body in an outward direction of the X-ray detector.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Hereinafter, exemplary embodiments will be described in detail with reference to the accompanying drawings. In the following description, the terms "front end", "back end", "upper part", "lower part", "top end", and "bottom end" are defined based on the drawings, and do not intend to limit shapes and locations of individual components.

Figure 1:
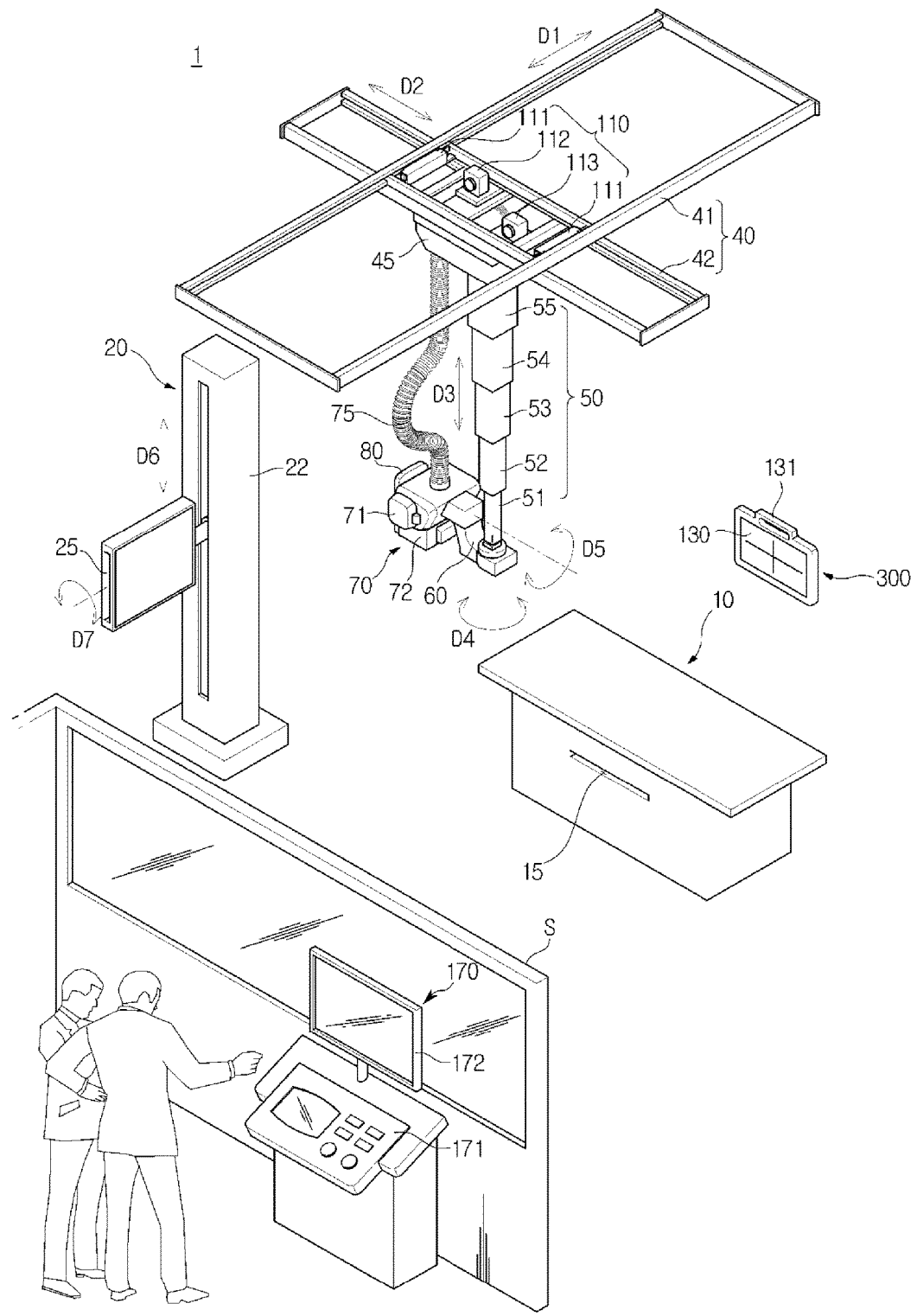
FIG. 1 is a perspective view of an X-ray imaging apparatus, according to an exemplary embodiment.
Figure 2:
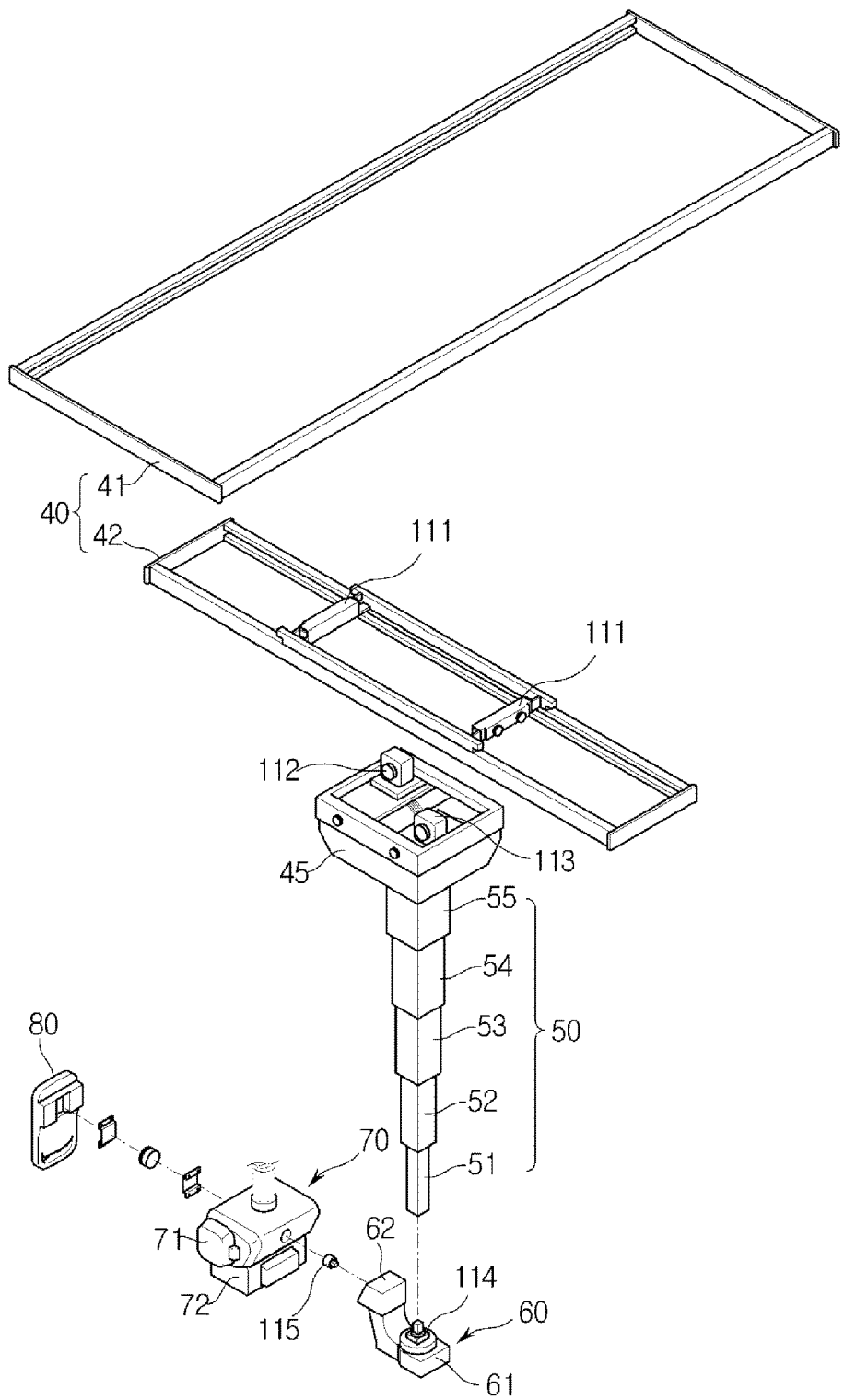
FIG. 2 is an exploded perspective view of an X-ray imaging apparatus, according to an exemplary embodiment.
Figure 3:
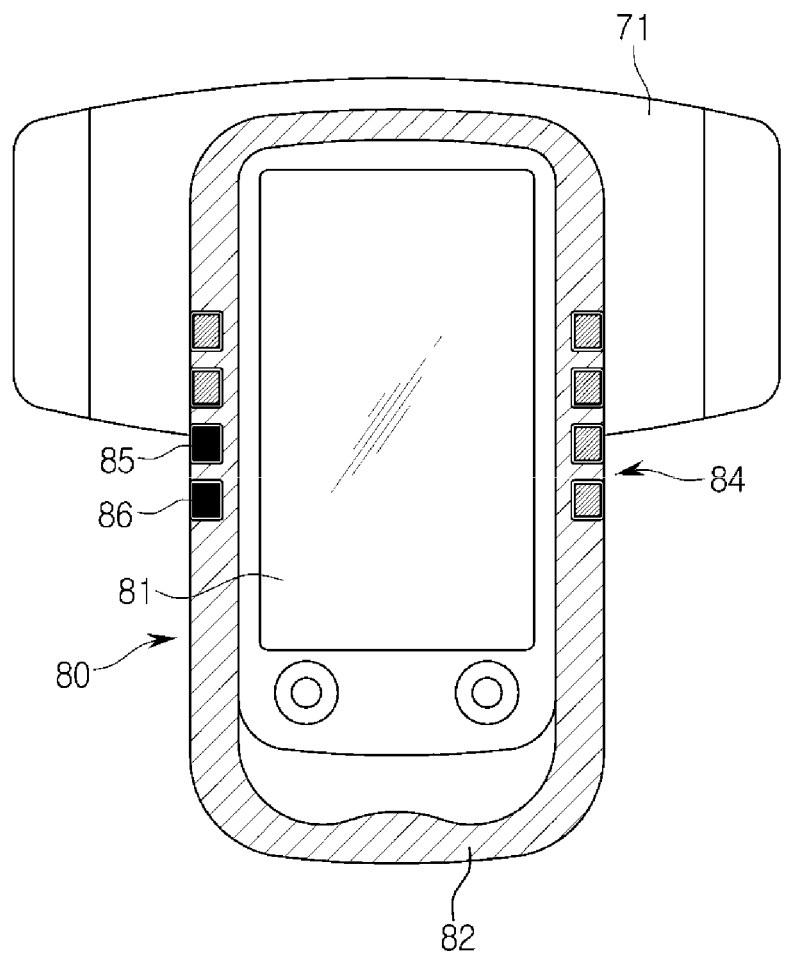
FIG. 3 is a front view of a control unit of an X-ray imaging apparatus, according to an exemplary embodiment.

FIG. 1 is a perspective view of an X-ray imaging apparatus according to an exemplary embodiment, FIG. 2 is an exploded perspective view of the X-ray imaging apparatus according to an exemplary embodiment, and FIG. 3 is a front view of a control unit of the X-ray imaging apparatus according to an exemplary embodiment.

As shown in FIGS. 1, 2, and 3, an X-ray imaging apparatus 1 may include a guide rail unit 40, a moving carriage 45, a post frame 50, a motor unit 110, an X-ray source 70, an X-ray detector 300, a control unit (also referred to herein as a "controller") 80, and a workstation 170. The X-ray imaging apparatus 1 may further include a radiography table 10 and a radiography stand 20 in which the X-ray detector 300 can be installed.

The guide rail unit 40, the moving carriage 45, and the post frame 50 may be used to move the X-ray source 70 toward an object.

The guide rail unit 40 may include a first guide rail 41 and a second guide rail 42 that are arranged to form a predetermined angle with respect to each other. The first guide rail 41 may be orthogonal to the second guide rail 42.

The first guide rail 41 may be installed on a ceiling of an examination room where the X-ray imaging apparatus 1 is placed.

The second guide rail 42 may be disposed beneath the first guide rail 41, and may be configured to slide with respect to the first guide rail 41. The first guide rail 41 may include a plurality of rollers (not shown) that are movable along the first guide rail 41. The second guide rail 42 may connect to the rollers and move along the first guide rail 41.

A longitudinal direction in which the first guide rail 41 extends is defined as a first direction D1, and a longitudinal direction in which the second guide rail 42 extends is defined as a second direction D2. Accordingly, the first direction D1 may be orthogonal to the second direction D2, and the first and second directions D1 and D2 may be parallel to the plane formed by the ceiling of the examination room.

The moving carriage 45 may be disposed beneath the second guide rail 42, and move along the second guide rail 42. The moving carriage 45 may include a plurality of rollers (not shown) to facilitate movement along the second guide rail 42. Accordingly, the moving carriage 45 is movable in the first direction D1 together with the second guide rail 42, and movable in the second direction D2 along the second guide rail 42. The post frame 50 may be fixed on the moving carriage 45 and disposed below the carriage 45. The post frame 50 may include a plurality of posts 51, 52, 53, 54, and 55.

The posts 51, 52, 53, 54, and 55 may connect to each other such that they can be folded with each other or nested together. The length of the post frame 50 fixed on the moving carriage 45 may increase or decrease in the elevation direction of the examination room.

A direction in which the length of the post frame 50 increases or decreases is defined as a third direction D3. Accordingly, the third direction D3 may be orthogonal to the first direction D1 and the second direction D2.

The X-ray source 70 may irradiate X-rays toward an object. Herein, the object may be a human's or animal's living body, however, the object is not limited to these. In this aspect, the object may include anything whose inside structure can be imaged by the X-ray imaging apparatus 1.

The X-ray source 70 may include an X-ray tube 71 which is configured to generate X-rays, and a collimator 72 which is configured to guide the generated X-rays to be directed toward an object. The X-ray tube 71 will be described in more detail below.

A revolute joint 60 may be disposed between the X-ray source 70 and the post frame 50.

The revolute joint 60 may couple the X-ray source 70 with the post frame 50, and support a load applied to the X-ray source 70.

The revolute joint 60 may include a first revolute joint 61 connected to the lower post 51 of the post frame 50, and a second revolute joint 62 connected to the X-ray source 70.

The first revolute joint 61 is rotatable with respect to the central axis of the post frame 50 extending in the elevation direction of the examination room. Accordingly, the first revolute joint 61 may rotate on a plane that is perpendicular to the third direction D3. The rotation direction of the first revolute joint 61 is defined as a fourth direction D4, and the fourth direction D4 is a rotation direction of an axis that is parallel to the third direction D3.

The second revolute joint 62 is rotatable on a plane that is perpendicular to the ceiling of the examination room. Accordingly, the second revolute joint 62 may rotate in a rotation direction of an axis that is parallel to the first direction D1 or the second direction D2. The rotation direction of the second rotation joint 62 is defined as a fifth direction D5, and the fifth direction D5 is a rotation direction of an axis extending in the first direction D1 or the second direction D2. The X-ray source 70 may connect to the revolute joint 60 and rotate in the fourth direction D4 and the fifth direction D5. In addition, the X-ray source 70 may connect to the post frame 50 through the revolute joint 60, and linearly move in any or all of the first direction D1, in the second direction D2, and in the third direction D3.

In order to facilitate a movement of the X-ray source 70 in the first direction D1 through the fifth direction D5, the motor unit 110 may be used. The motor unit 110 may be electrically driven, and may include encoders.

The motor unit 110 may include a first motor 111, a second motor 112, a third motor 113, a fourth motor 114, and a fifth motor 115 that correspond to the first direction D1, the second direction D2, the third direction D3, the fourth direction D4, and the fifth direction D5, respectively.

The first to fifth motors 111 to 115 may be arranged at appropriate respective locations in consideration of convenience of design. For example, the first motor 111 that is used to move the second guide rail 42 in the first direction D1 may be disposed within close proximity of the first guide rail 41, the second motor 112 that is used to move the moving carriage 45 in the second direction D2 may be disposed within close proximity of the second guide rail 42, and the third motor 113 that is used to increase or decrease the length of the post frame 50 in the third direction D3 may be disposed in the moving carriage 45. Further, the fourth motor 114 that is used to rotate the X-ray source 70 in the fourth direction D4 may be disposed within close proximity of the first revolute joint 61, and the fifth motor 115 that is used to rotate the X-ray source 70 in the fifth direction D5 may be disposed within close proximity of the second revolute joint 62.

The motor unit 110 may connect to power transfer means (not shown) in order to cause linear movement and/or rotation of the X-ray source 70 in the first to fifth directions D1 to D5. The power transfer means may include any one or more of a belt and a pulley, a chain and a sprocket, or a shaft.

In one side of the X-ray source 70, the control unit 80 may be disposed to provide a user interface. The typical user is a person who diagnoses an object by using the X-ray imaging apparatus 1, and may be a medical staff member including any of a doctor, a radiological technologist, and a nurse. However, the user is not limited to the above-mentioned persons, and may include anyone who uses the X-ray imaging apparatus 1.

The control unit 80 may include, as illustrated in FIG. 3, a first display unit 81 and a plurality of buttons 84 to enable a user to input various kinds of information for radiography or to manipulate individual units. The first display unit 81 may be implemented as any of a Cathode Ray Tube (CRT), a Liquid Crystal Display (LCD), or a Light Emitting Diode (LED) display. However, the first display unit 81 is not limited to the above-mentioned types of display devices.

The buttons 84 may include a fourth directional rotation selection button 85, which relates to controlling a rotation of the X-ray source 70 in the fourth direction D4, and a fifth directional rotation selection button 86, which relates to controlling a rotation of the X-ray source 70 in the fifth direction D5. In this aspect, when a user wants to rotate the X-ray source 70 in the fourth direction D4, the user may cause the X-ray source 70 to rotate in the fourth direction D4 after pressing the fourth directional rotation selection button 85. When the user wants to rotate the X-ray source 70 in the fifth direction D5, the user may cause the X-ray source 70 to rotate in the fifth direction D5 after pressing the fifth directional rotation selection button 86 or while pressing the fifth directional rotation selection button 86. The locations of the fourth and fifth directional rotation selection buttons 85 and 86 shown in FIG. 3 are exemplary, and the fourth and fifth directional rotation selection buttons 85 and 86 may be arranged at different locations.

Further, the control unit 80 may include a handle 82 that the user can grip. The user may grip the handle 82 of the control unit 80 in order to apply power or torque, thereby causing the X-ray source 70 to move. This is defined as a manual move mode. Movement of the X-ray source 70 may be controlled by a motor controller (not shown), which is defined as an automatic move mode. In FIG. 3, the handle 82 is provided in the lower part of the control unit 80, however, the handle 82 may be provided at another location.

The X-ray detector 300 may detect X-rays which have propagated through the object. In the front side of the X-ray detector 300, an incident surface 130 onto which X-rays are incident may be provided, and a sensing panel (also referred to herein as a "sensor panel") 330 (see FIG. 5) may be installed in the X-ray detector 300. In the sensing panel 330, a plurality of pixels 150 (see FIG. 5) that respond to incident X-rays may be arranged in a matrix form. In the upper center part of the X-ray detector 300, a handle 131 may be provided so that the user can move or carry the X-ray detector 300.

The X-ray detector 300 may operate in any of various radiography modes in accordance with a positional configuration of the X-ray detector 300. In particular, the X-ray detector 300 may operate in a table mode when the X-ray detector 300 is installed in the radiography table 10, in a stand mode when the X-ray detector 300 is installed in the radiography stand 20, and in a portable mode when the X-ray detector 300 is positioned at an arbitrary location according to an object's location or an area to be photographed, without being installed in the radiography table 10 or the radiography stand 20. More particularly, accommodating slots into which the X-ray detector 300 can be inserted may be formed in the radiography table 10 and in the radiography stand 20. The accommodating slot formed in the radiography table 10 is defined as a first accommodating slot 15, and the accommodating slot formed in the radiography stand 20 is defined as a second accommodating slot 25. The second accommodating slot 25 is movable in the length direction of a support bar 22, and is rotatable in the rotation direction of an axis which is perpendicular to the length direction of the support bar 22, as illustrated in FIG. 1. The length direction of the support bar 22 is defined as a sixth direction D6, and the rotation direction of the axis which is perpendicular to the sixth direction D6 is defined as a seventh direction D7.

The workstation 170 may include an input unit 171 and a second display unit 172 in order to provide a user interface, similarly as the control unit 80. Accordingly, the user can input various kinds of information for radiography and/or manipulate individual units via the workstation 170. Further, the user may input various commands (e.g., a command for selecting a radiography location, a start command for radiography, etc.) related to operations of the X-ray imaging apparatus 1 via the workstation 170. In addition, the user may check images which are acquired during radiography via the workstation 170.

The input unit 171 may include at least one from among a switch, a keyboard, a trackball, a mouse, and a touch screen. If the input unit 171 is implemented as a Graphical User Interface (GUI) such as a touch screen, in other words, if the input unit 171 is implemented in software, the input unit 171 may be displayed through the second display unit 172. The second display unit 172 may include, similarly as the first display unit 81, any of a CRT, a LCD, or a LED display.

The workstation 170 may include any of various processors, such as a Central Processing Unit (CPU) or a Graphics Processing Unit (GPU), and a Printed Circuit Board (PCB), and may further include various kinds of storage units as necessary. Accordingly, the workstation 170 may accommodate main components (e.g., a controller) of the X-ray imaging apparatus 1 which are configured to make determinations for operations of the X-ray imaging apparatus 1 or to generate various control signals.

The workstation 170 may be placed in an independent space S from which X-rays can be blocked, and may be connected to the X-ray source 70 and the X-ray detector 300 via wired and/or wireless communication.

Figure 4:
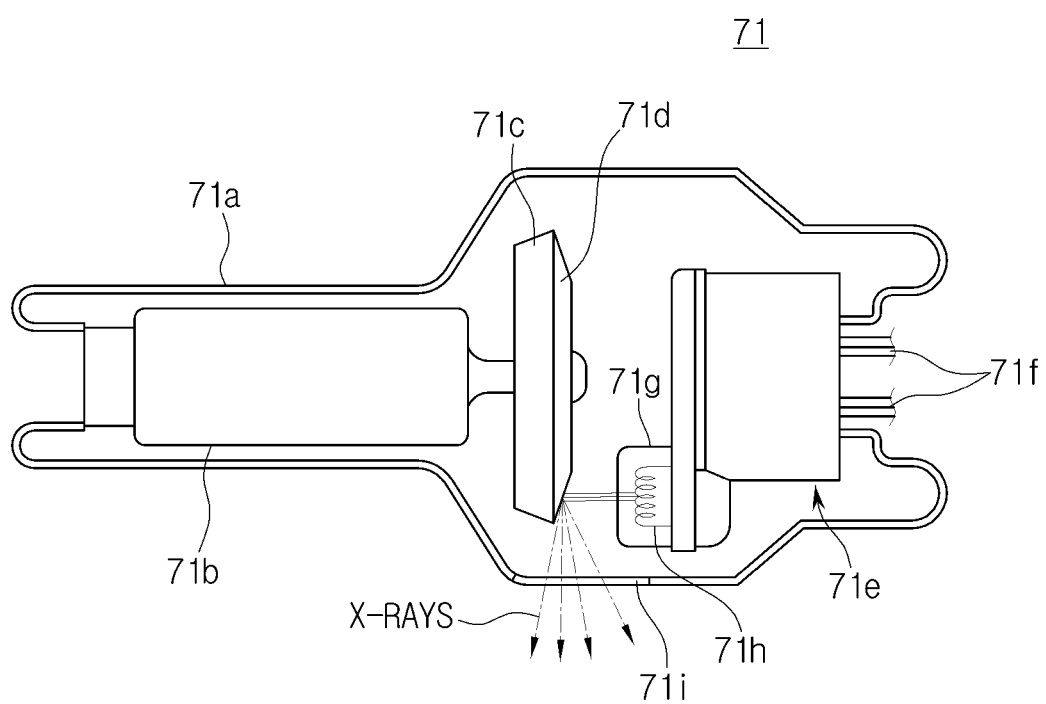
FIG. 4 is a cross-sectional view showing an internal structure of an X-ray tube included in an X-ray imaging apparatus, according to an exemplary embodiment.

The X-ray source 70 may generate X-rays, and irradiate the generated X-rays to an object. In order to generate X-rays, the X-ray source 70 may include an X-ray tube 71 as shown in FIG. 4. FIG. 4 illustrates an example of an internal structure of the X-ray tube 71.

The X-ray tube 71 may be embodied as a two-electrode vacuum tube which includes an anode 71c and a cathode 71e. The body of the two-electrode vacuum tube may be implemented as a glass tube 71a made of silica hard glass or the like.

The cathode 71e may include a filament 71h and a focusing electrode 71g configured for focusing electrons, and the focusing electrode 71g is also called a focusing cup. The inside of the glass tube 71a may be evacuated to a high vacuum state of approximately 10 mm Hg, and the filament 71h of the cathode 71e may be heated to a high temperature, thereby generating thermoelectrons. The filament 71h may be a tungsten filament, for example, and the filament 71h may be heated by applying a current to electrical leads 71f connected to the filament 71h. However, instead of the filament 71h, a carbon nano-tube which is capable of being driven with high-speed pulses may be used as the cathode 71e.

The anode 71c may be made of copper, for example, and a target material 71d may be applied on the surface of the anode 71c that faces the cathode 71e, wherein the target material 71d may include a high-resistance material, e.g., any of Cr, Fe, Co, Ni, W, or Mo. The higher the melting point of the target material 71d, the smaller the focal spot size.

When a relatively high voltage is applied between the cathode 71e and the anode 71c, thermoelectrons may be accelerated and collide with the target material 71d of the anode 71e, thereby generating X-rays. The X-rays may be irradiated to the outside through a window 71i. The window 71i may be a beryllium (Be) thin film.

The target material 71d may be rotated by a rotor 71b. When the target material 71d rotates, the heat accumulation rate may increase by a factor of 10 times per unit area and the focal spot size may be reduced, as compared to when the target material 71d is fixed.

The voltage that is applied between the cathode 71e and the anode 71c of the X-ray tube 71 is called a tube voltage. The magnitude of a tube voltage may be expressed as a crest value (kVp). When the tube voltage increases, a velocity of thermoelectrons may increase accordingly. Then, energy (i.e., photonic energy) of X-rays that are generated when the thermoelectrons collide with the target material 71d may also increase. A current that flows through the X-ray tube 71 is called a tube current, and can be expressed as an average value (e.g., in milliamperes (mA)). When a tube current increases, a dose of X-rays (that is, the number of X-ray photons) may increase. In summary, an energy level of X-rays can be controlled by adjusting a tube voltage. In addition, a dose of X-rays can be controlled by adjusting a tube current and an X-ray exposure time.

The X-ray detector 300 may detect X-rays irradiated by the X-ray source 70 which have then propagated through an object. The X-rays may be detected by the sensing panel 330 installed in the X-ray detector 300. The sensing panel 330 may convert the detected X-rays into electrical signals, and acquire an image that relates to the inside of the object.

The sensing panel 330 can be classified according to its material configuration, a method of converting detected X-rays into electrical signals, and a method of acquiring image signals.

The sensing panel 330 is classified into a mono type device or a hybrid type device according to its material configuration.

If the sensing panel 330 is a mono type device, a part which is configured for detecting X-rays and generating electrical signals and a part which is configured for reading and processing the electrical signals may be semiconductors made of the same material, or may be manufactured by one process. In this case, the sensing panel 330 may include a Charge Coupled Device (CCD) or a Complementary Metal Oxide Semiconductor (CMOS) which is a light receiving device.

If the sensing panel 330 is a hybrid type device, a part which is configured for detecting X-rays and generating electrical signals and a part which is configured for reading and processing the electrical signals may be made of different materials, or may be manufactured by different processes. For example, there are cases of detecting X-rays by using a light receiving device, such as a photodiode, a CCD, or CdZnTe, and reading and processing electrical signals by using a CMOS Read Out Integrated Circuit (CMOS ROIC), of detecting X-rays by using a strip detector, and reading and processing electrical signals by using a CMOS ROIC, and of using an a-Si or a-Se flat panel system.

The X-ray detector 300 may use a direct conversion mode and an indirect conversion mode according to a method of converting X-rays into electrical signals.

In the direct conversion mode, if X-rays are irradiated, electron-hole pairs are temporarily generated in a light receiving device, electrons move to an anode, and holes move to a cathode due to an electric field which is applied to both terminals of the light receiving device. The sensing panel 330 converts the movements of the electrons and holes into electrical signals. The light receiving device may be made of any of a-Se, CdZnTe, $HgI_2$, or $PbI_2$, for example.

In the indirect conversion mode, if X-rays irradiated from the X-ray source 70 react with a scintillator to emit photons having a wavelength of a visible light region, the light receiving device detects the photons and then converts the photons into electrical signals. The light receiving device may be made of a-Si, for example, and the scintillator may include any of a GADOX scintillator of a thin film type, or a CSI (TI) of a micro pillar type or a needle type.

The sensing panel 330 may use a Charge Integration Mode (CIM) which corresponds to storing charges for a predetermined time period and then acquiring a signal from the stored charges, or a Photon Counting Mode (PCM) which corresponds to counting the number of photons whenever a signal is generated by single X-ray photons, according to a method of acquiring electrical signals.

The material configuration of the sensing panel 330 and the signal conversion method of the sensing panel 330 are not limited, however, for convenience of description, in an exemplary embodiment which will be described below, the sensing panel 330 uses the direct conversion mode of acquiring electrical signals directly from X-rays, and the sensing panel 330 is a hybrid type in which a sensor chip for detecting X-rays is integrated with a read circuit chip and the PCM.

Figure 5:
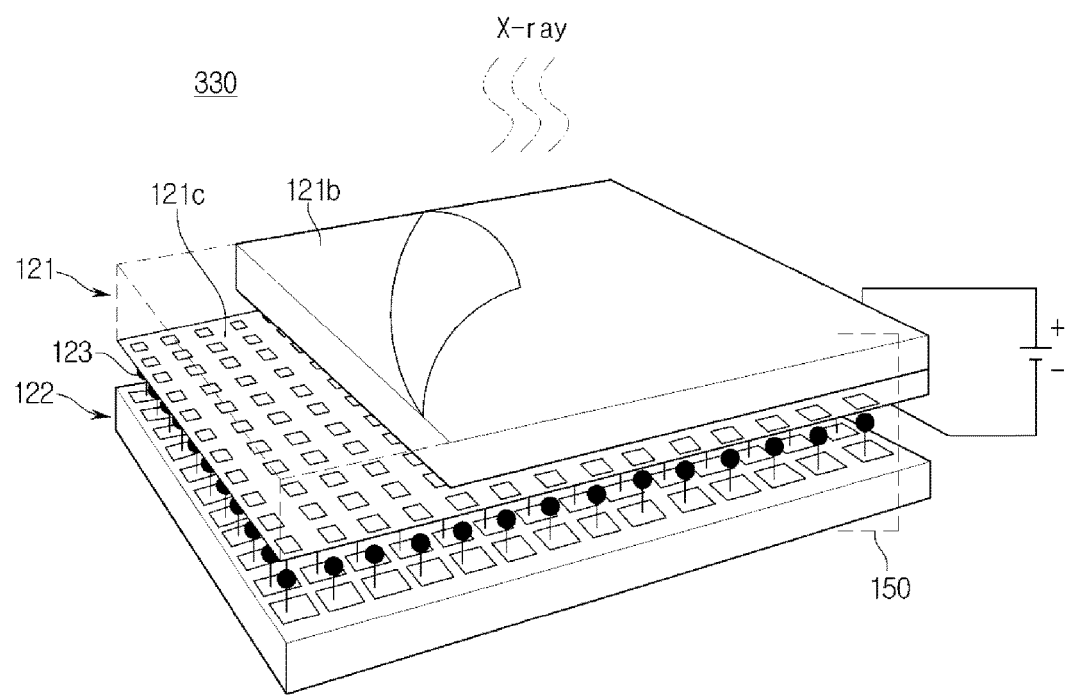
FIG. 5 schematically shows a structure of a sensing panel included in an X-ray imaging apparatus, according to an exemplary embodiment.

The sensing panel 330 may have a 2-dimensional (2D) array structure that includes a plurality of pixels 150, as shown in FIG. 5. FIG. 5 schematically illustrates a structure of the sensing panel 330.

Referring to FIG. 5, the sensing panel 330 may include a light receiving device 121 which is configured to detect X-rays and to convert the X-rays into electrical signals, and a read circuit 122 which is configured to read out the electrical signals.

The light receiving device 121 may be made of a single crystal semiconductor material in order to ensure high resolution, high response speed, and a high dynamic area even under conditions of low energy and a small dose of X-rays. The single crystal semiconductor material may include any of Ge, CdTe, CdZnTe, or GaAs.

The light receiving device 121 may be in the form of a PIN photodiode. The PIN photodiode may be fabricated by bonding a p-type semiconductor substrate 121c in the form of a 2D array on the lower surface of an n-type semiconductor substrate 121b which has a relatively high resistance.

The read circuit 122, which is fabricated according to a Complementary Metal Oxide Semiconductor (CMOS) process, may form a 2D array structure, and may be coupled with the p-type substrate 121c of the light receiving device 121 in units of pixels 150. The CMOS read circuit 122 and the light receiving device 121 may be coupled by a Flip-Chip Bonding (FCB) method. More specifically, the CMOS read circuit 122 and the light receiving device 121 may be coupled by forming bumps 123 with PbSn, In, or the like, reflowing, applying heat, and then compressing.

Figure 6:
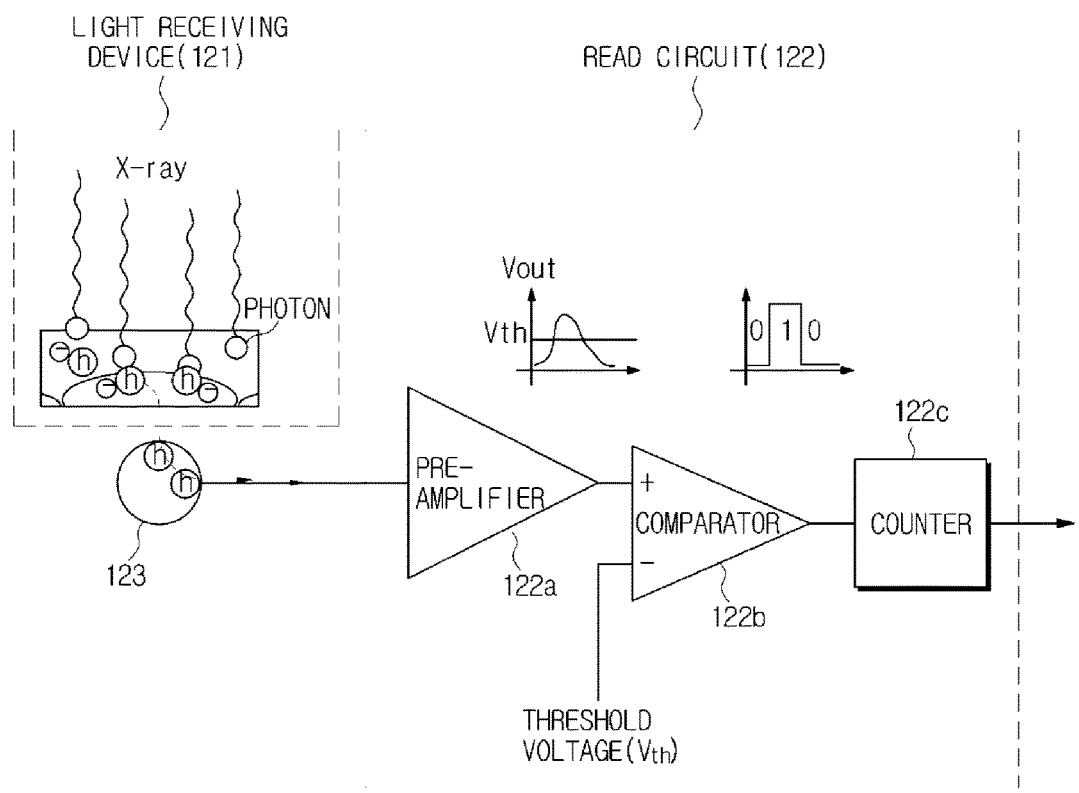
FIG. 6 is a circuit diagram schematically showing a pixel area of the sensing panel shown in FIG. 5.

FIG. 6 is a circuit diagram which schematically illustrates a pixel area of the sensing panel 330 shown in FIG. 5.

Referring to FIG. 6, if photons of X-rays are incident to the light receiving device 121, electrons existing in a valence band may receive the energy of the photons to be excited to a conduction band over an energy gap of a band gap. Thereby, electron-hole pairs may be generated in a depletion region within which neither electrons nor holes exist.

If a reverse bias is applied after metal electrodes are respectively formed on the p-type layer and the n-type substrate of the light receiving device 121, electrons in the electron-hole pairs generated in the depletion region may move to the n-type region, and holes in the electron-hole pairs may move to the p-type region. The holes moved to the p-type region may be input to the read circuit 122 through the bumps 123.

Charges input to the read circuit 122 may be transferred to a pre-amplifier 122a, and the pre-amplifier 122a may output a voltage signal that corresponds to the charges.

The voltage signal output from the pre-amplifier 122a may be transferred to a comparator 122b. The comparator 122b may compare the voltage signal to a predetermined threshold voltage that can be controlled by an external device, in order to output a pulse signal of "1" or "0" as the result of the comparison. More specifically, if a voltage of the voltage signal is greater than the predetermined threshold voltage, the comparator 122b may output a signal of "1", and if the voltage of the voltage signal is smaller than the predetermined threshold voltage, the comparator 122b may output a signal of "0". The counter 122c may count the number of times a signal of "1" has been generated, and output the count value as digital data.

Figure 7:
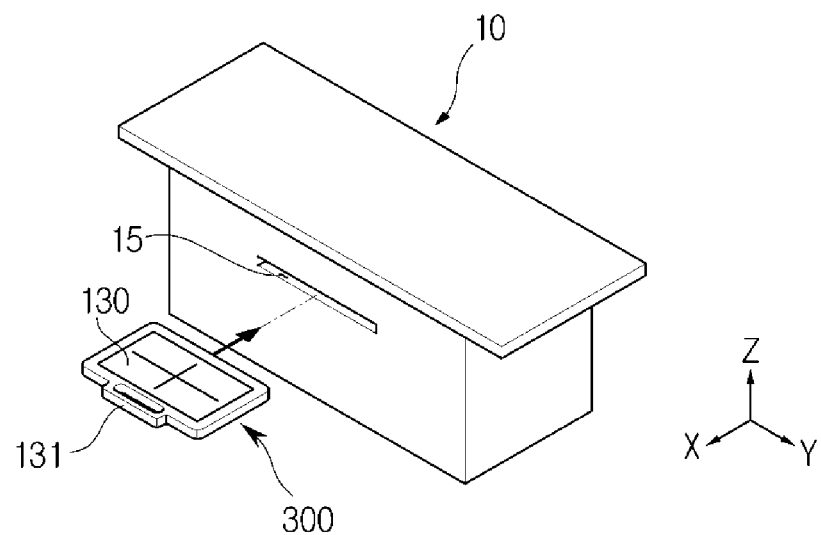
FIG. 7 is a view for describing a method in which an X-ray detector of an X-ray imaging apparatus according to an exemplary embodiment is installed in a radiography table.
Figure 7:
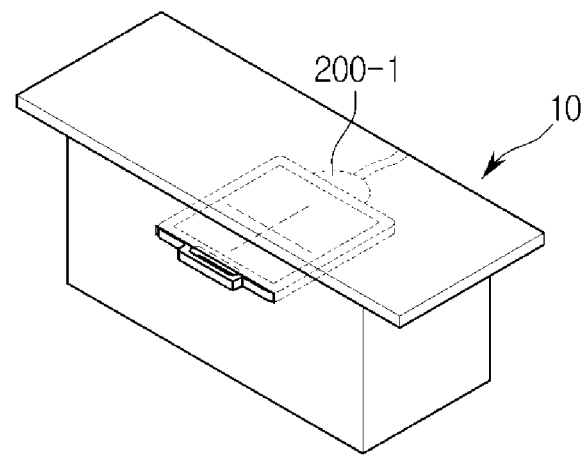

As described above, the X-ray detector 300 may operate in the table mode, in the stand mode, or in the portable mode in order to detect X-rays. The locations of the X-ray detector 300 in the individual radiography modes will be described with reference to FIGS. 7, 8, and 9, below. FIG. 7 is a view for describing a method in which the X-ray detector 300 of the X-ray imaging apparatus 1 according to an exemplary embodiment is installed in a radiography table, FIG. 8 is a view for describing a method in which the X-ray detector 300 of the X-ray imaging apparatus 1 according to an exemplary embodiment is installed in a radiography stand, and FIG. 9 shows a case in which the X-ray detector 300 of the X-ray imaging apparatus 1 according to an exemplary embodiment is used in a portable mode.

A plurality of coupling modules 200 may be provided to correspond to the respective radiography modes. Referring to FIGS. 7, 8, and 9, the coupling modules 200 may include a table coupling module 200-1 which corresponds to the table mode, a stand coupling module 200-2 which corresponds to the stand mode, and a portable coupling module 200-3 which corresponds to the portable mode. However, the locations and numbers of the coupling modules 200 are only exemplary. In particular, only the table coupling module 200-1 and the stand coupling module 200-2 may be provided, or four coupling modules or more may be provided. In the current exemplary embodiment, it is assumed that the coupling modules 200 include the table coupling module 200-1, the stand coupling module 200-2, and the portable coupling module 200-3.

Referring to FIG. 7, the table coupling module 200-1 may be installed in the first accommodation slot 15. In order to perform radiography on an object that lies on the radiography table 10, the X-ray detector 300 may be installed in the radiography table 10. More specifically, the X-ray detector 300 may be inserted into the first accommodating slot 15 formed in the radiography table 10. When the X-ray detector 300 is inserted into the first accommodating slot 15, the X-ray detector 300 may be inserted in a state of being parallel to a bottom plane, that is, a plane formed by x- and y-axes, as illustrated in drawing (a) in the top portion of FIG. 7. After the X-ray detector 300 is inserted into the first accommodating slot 15, the X-ray detector 300 may be maintained in the state of being parallel to the bottom plane or the plane formed by the x-axis and the y-axis, as illustrated in drawing (b) in the bottom portion of FIG. 7. Further, the X-ray detector 300 inserted into the first accommodating slot 15 may be connected to the table coupling module 200-1. As such, a state in which the X-ray detector 300 has been inserted into the first accommodating slot 15 and coupled with the table coupling module 200-1 is the table mode.

Figure 8:
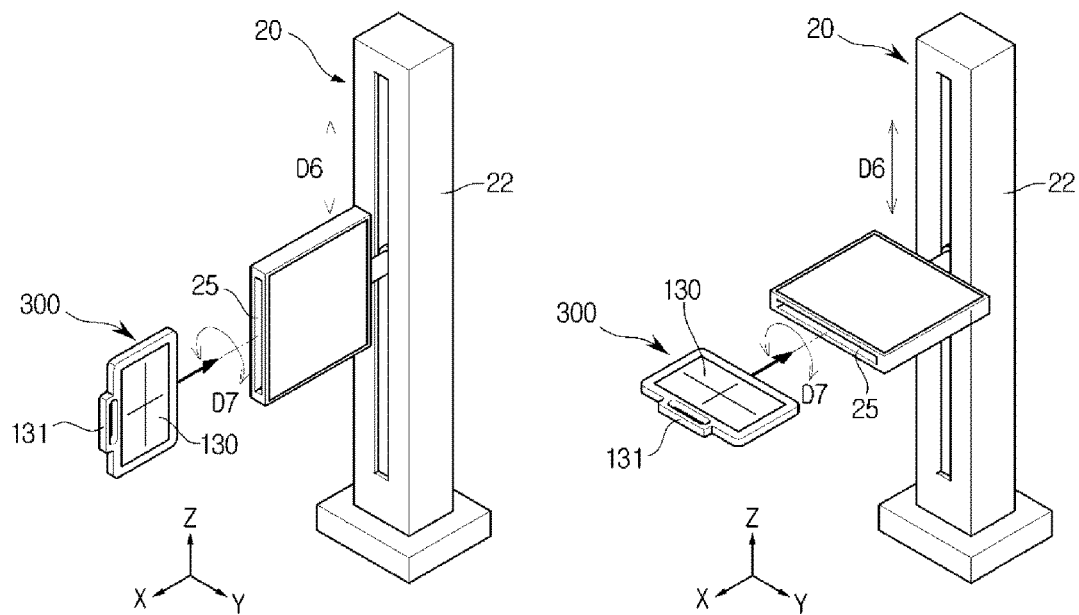
FIG. 8 is a view for describing a method in which an X-ray detector of an X-ray imaging apparatus according to an exemplary embodiment is installed in a radiography stand.
Figure 8:
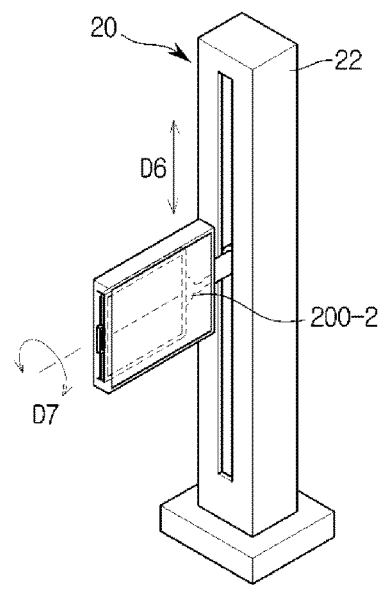
Figure 9:
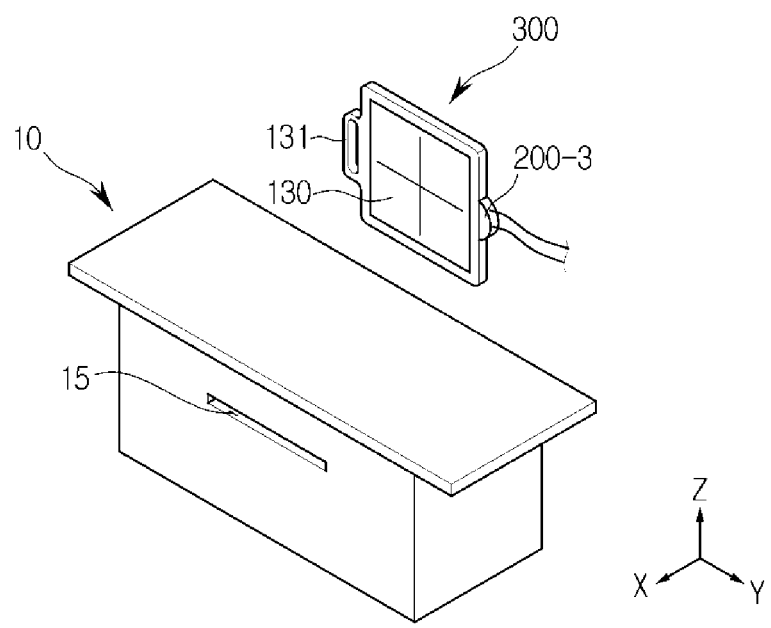
FIG. 9 shows a case in which an X-ray detector of an X-ray imaging apparatus according to an exemplary embodiment is used in a portable mode.

Referring to FIG. 8, the stand coupling module 200-2 may be installed in the second accommodation slot 25. In order to perform radiography on an object that stands in front of the radiography stand 20, the X-ray detector 300 may be installed in the radiography stand 20. More specifically, the X-ray detector 300 may be inserted into the second accommodating slot 25 formed in the radiography stand 20. Because the second accommodating slot 25 is rotatable in the seventh direction D7, the X-ray detector 300 may be inserted into the second accommodating slot 25 in a state of being perpendicular to a bottom plane or parallel to a plane formed by the x-axis and the z-axis, as illustrated in the left side of drawing (a) in the top portion of FIG. 8, or the X-ray detector 300 may be inserted into the second accommodating slot 25 in a state of being parallel to the bottom plane or parallel to a plane formed by the x-axis and the y-axis, as illustrated in the right side of drawing (a) of FIG. 8. After the X-ray detector 300 is inserted into the second accommodating slot 25, the second accommodating slot 25 may rotate so that the X-ray detector 300 is maintained in a state of being perpendicular to the bottom plane, that is, parallel to the plane formed by the x-axis and the z-axis, as illustrated in drawing (b) in the bottom portion of FIG. 8. Further, the X-ray detector 300 inserted into the second accommodating slot 25 may be connected to the stand coupling module 200-2. As such, a state in which the X-ray detector 300 has been inserted into the second accommodating slot 25 and coupled with the stand coupling module 200-2 is the stand mode.

In order to perform radiography on a moving object, as well as an object that lies or stands, the X-ray detector 300 may be in a portable state, instead of being inserted into the radiography table 10 or the radiography stand 20. This state is the portable mode. As shown in FIG. 9, in the portable mode, the X-ray detector 300 may be coupled with the portable coupling module 200-3, and the portable coupling module 200-3 may be placed at an arbitrary location at which radiography can be easily performed in the portable mode. For example, as illustrated in FIG. 9, the portable coupling module 200-3 may be placed in the backside of the top plate of the radiography table 10.

Figure 10:
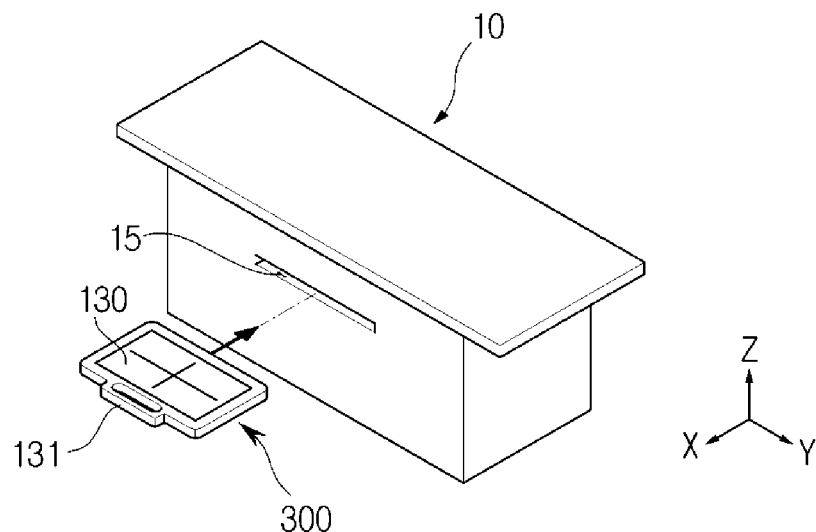
FIGS. 10, 11, and 12 show other examples relating to positions of a table coupling module, a stand coupling module, and a portable coupling module, in an X-ray imaging apparatus, according to an exemplary embodiment.
Figure 10:
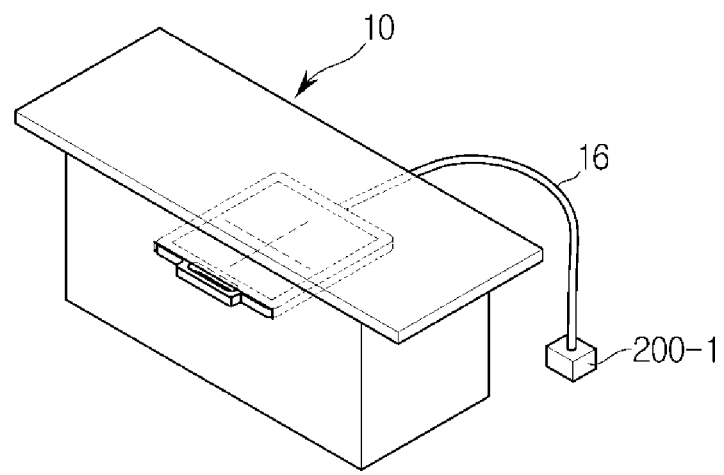
Figure 11:
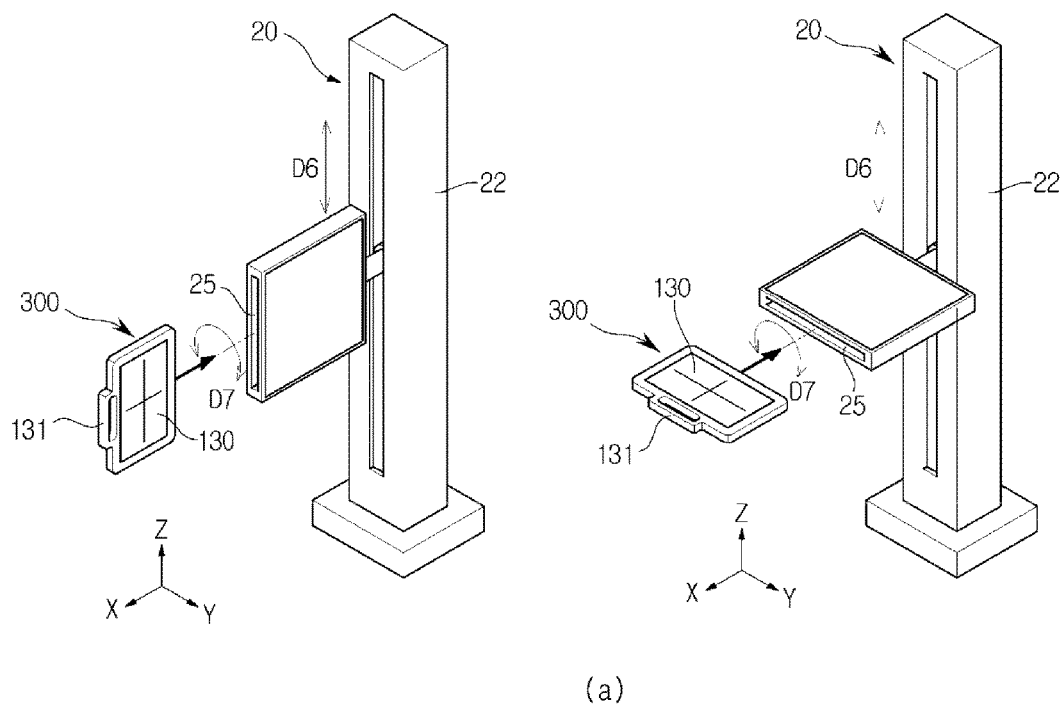
Figure 11:
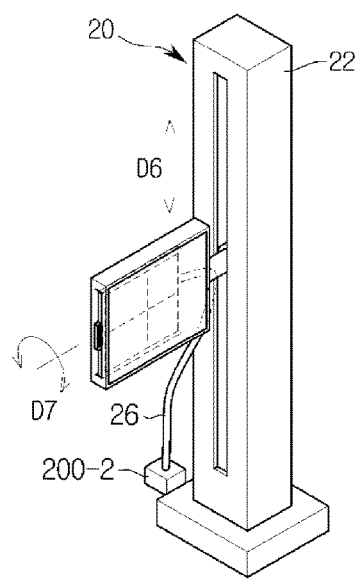
Figure 12:
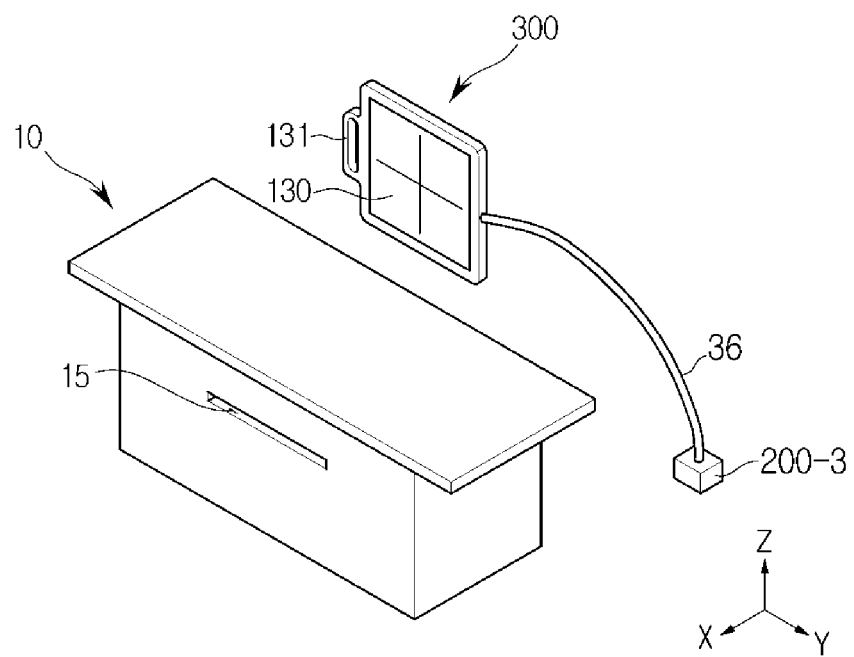

FIGS. 10, 11, and 12 show other examples which relate to positions of the table coupling module 200-1, the stand coupling module 200-2, and the portable coupling module 200-3, in the X-ray imaging apparatus 1 according to an exemplary embodiment.

Referring to FIG. 10, the table coupling module 200-1 may be located outside the first accommodation slot 15, and coupled with the X-ray detector 300 inserted in the first accommodation slot 15 via a cable 16. The table coupling module 200-1 may be located adjacent to the radiography table 10 in order to be coupled with the X-ray detector 300.

Referring to FIG. 11, the stand coupling module 200-2 may be located outside the second accommodation slot 25, and coupled with the X-ray detector 300 inserted in the second accommodation slot 25 via a cable 26. The stand coupling module 200-2 may be located adjacent to the radiography stand 20 in order to be coupled with the X-ray detector 300.

Referring to FIG. 12, the portable coupling module 200-3 may be coupled with the X-ray detector 300 via a cable 36, in the portable mode.

Further, if the X-ray detector 300 receives a supply voltage in a wired fashion and is connected to a workstation in a wired fashion, each coupling module 200 may function to connect the X-ray detector 300 to an external power supply and a network hub. Alternatively, each coupling module 200 may be implemented as a board on which electrical devices are mounted, separately from a configuration of connecting the X-ray detector 300 to an external power supply and a network hub. Hereinbelow, a configuration of the coupling module 200 will be described in detail.

First, a case in which the coupling module 200 includes a configuration of connecting the X-ray detector 300 to an external power supply and a network hub will be described. In this case, the coupling module 200 may be called a power box. However, the coupling module 200 is defined by its configuration and operation, not by its name.

Figure 13:
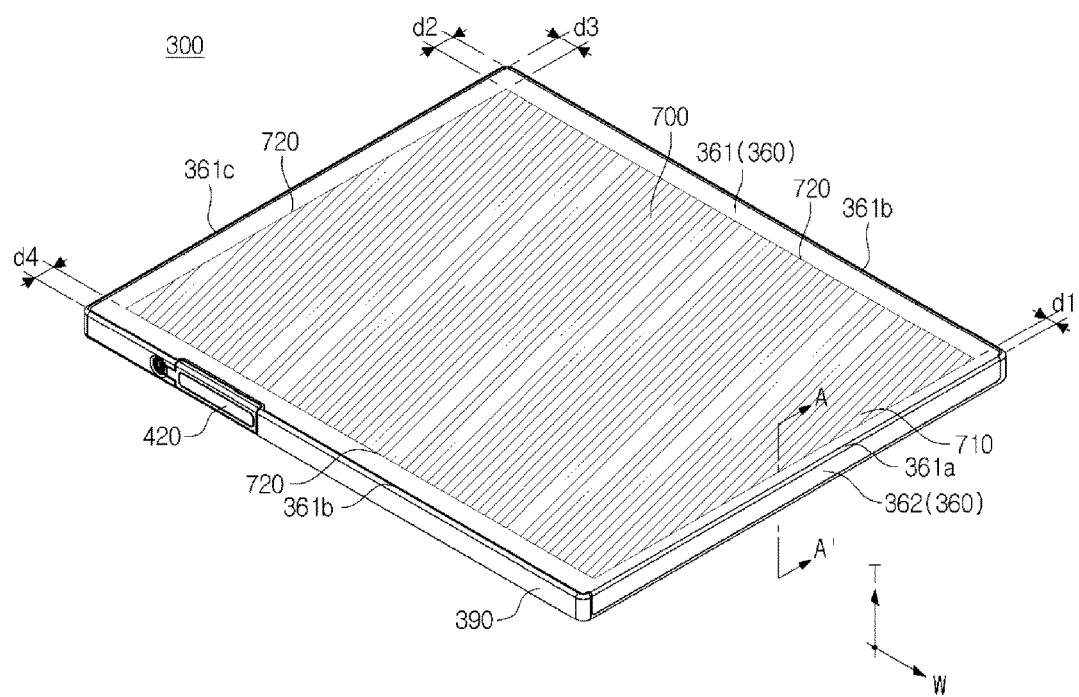
FIG. 13 is a perspective view of an X-ray detector of an X-ray imaging apparatus, according to an exemplary embodiment.
Figure 14:
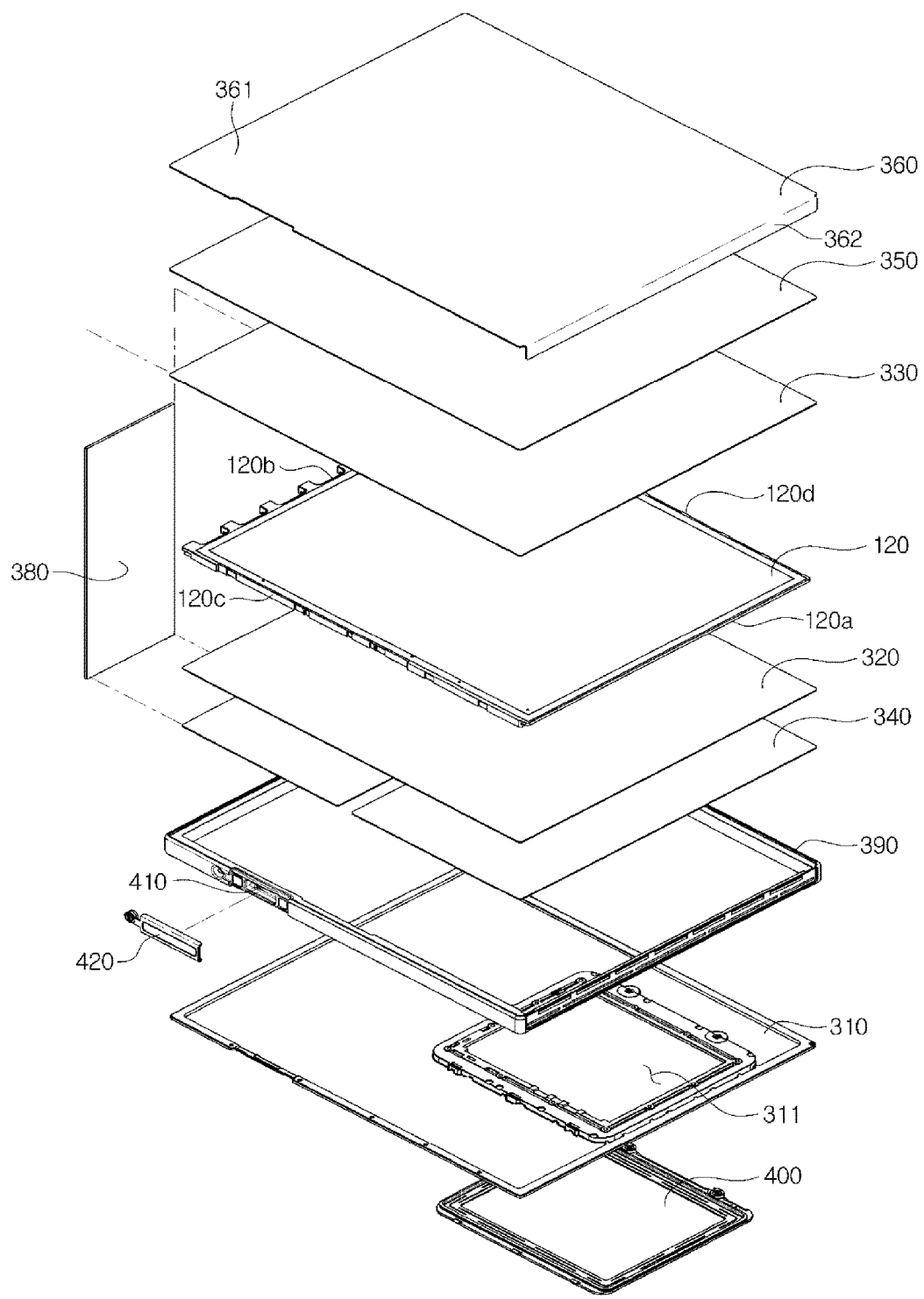
FIG. 14 is an exploded perspective view of an X-ray detector of an X-ray imaging apparatus, according to an exemplary embodiment.

FIG. 13 is a perspective view of the X-ray detector 300 of the X-ray imaging apparatus 1 according to an exemplary embodiment, and FIG. 14 is an exploded perspective view of the X-ray detector 300 of the X-ray imaging apparatus 1 according to an exemplary embodiment. In FIGS. 13 to 24, a case in which an active area 700 is wider than a typical active area and biased with respect to the X-ray detector 300 will be described. In the following description, T represents a thickness direction of the X-ray detector 300, and W represents a width direction of the X-ray detector 300.

As shown in FIGS. 13 and 14, the X-ray detector 300 may be used to detect X-rays which have been irradiated from the X-ray source 70 (see FIGS. 1 and 2). The X-ray detector 300 may include an insulating substrate 320. The X-ray detector 300 may further include a middle block 120. The X-ray detector 300 may further include a sensing panel 330. The X-ray detector 300 may further include a scintillator 350. The X-ray detector 300 may further include a circuit board 340. The insulating substrate 320 may support the middle block 120 and the sensing panel 330. The middle block 120 may rest on one surface of the insulating substrate 320, and the circuit board 340 may rest on the opposite surface of the insulating substrate 320. The sensing panel 330 may rest on one surface of the middle block 120.

The scintillator 350 may include phosphors. The scintillator 350 may convert incident X-rays into visible light. A cover (not shown) for protecting the scintillator 350 may be provided on one surface of the scintillator 350. The scintillator 350 may be made of a metal material, such as, for example, aluminum.

On the upper surface of the scintillator 350, a top frame 360 may be positioned. The top frame 360 may include any of a carbon plate, a melamine plate, or a polycarbonate plate. On one surface of the top frame 360, a deco sheet (not shown) may be provided.

The sensing panel 330 may include a plurality of pixels 150 (see FIG. 5), and each pixel 150 may include a photoelectric conversion device, such as a thin-film transistor, a photodiode, and/or the like. The sensing panel 330 may read out an intensity of light which passes through the scintillator 350 in unit of pixels. The sensing panel 330 may include an electrical circuit which is configured to transfer outputs from the photoelectric conversion device to the outside.

The circuit board 340 may perform calculations for acquiring an image of an object using data that is acquired based on signals read by the sensing panel 330. The circuit board 340 may include a memory and a calculator. The memory may store shadow information of an object according to incident angles of X-rays, and the calculator may calculate an incident angle of X-rays, based on a shadow shape of the object formed on the sensing panel 330 and the shadow information stored in the memory. The memory and the calculator may be located outside the X-ray detector 300.

The sensing panel 330 may be electrically connected to the circuit board 340. The flexible printed circuit board 380 may include a read-out terminal (not shown) which is configured for reading out information of the sensing panel 330.

The middle block 120 may be disposed between the insulating substrate 320 and the sensing panel 330. The middle block 120 may be disposed in the X-ray detector 300 so as to support the sensing panel 330. In addition, the middle block 120 may be disposed in the X-ray detector 300 so as to support the scintillator 350 together with the sensing panel 330. The sensing panel 330 may rest on one surface of the middle block 120. The scintillator 350 may rest on one surface of the sensing panel 330. In this aspect, the scintillator 350 may be applied on the sensing panel 330. The sensing panel 330 on which the scintillator 350 is applied may be applied on the middle block 120.

The X-ray detector 300 may further include the top frame 360, a side frame 390, and a bottom frame 310 that are mutually coupled with each other to form an outer appearance of the X-ray detector 300. The top frame 360 may form a top appearance of the X-ray detector 300. The side frame 390 may form a side appearance of the X-ray detector 300. The bottom frame 310 may form a bottom appearance of the X-ray detector 300.

In the inside of the X-ray detector 300, an accommodation space may be formed. The insulating substrate 320, the middle block 120, the sensing panel 330, the scintillator 350, and the circuit board 340 may be accommodated in the accommodation space. In this aspect, the top frame 360, the side frame 390, and the bottom frame 310 may be coupled with each other to form an accommodation space in which the insulating substrate 320, the middle block 120, the sensing panel 330, the scintillator 350, and the circuit board 340 can be accommodated. In particular, the insulating substrate 320, the middle block 120, the sensing panel 330, the scintillator 350, and the circuit board 340 may be accommodated in the inside of the frames 360, 390, and 310. The insulating substrate 320, the middle block 120, the sensing panel 330, the scintillator 350, the circuit board 340, etc. may be protected from external impacts by the top frame 360, the side frame 390, and the bottom frame 310. The bottom frame 310 may be made of the same material as the top frame 360.

The X-ray detector 300 may further include a battery (not shown) that is accommodated in the accommodation space.

The X-ray detector 300 may further include a battery cover 400 which is configured to open or close a part of the accommodation space in order to separate the battery accommodated in the accommodation space. The battery cover 400 may be detachably coupled with the lower part of the bottom frame 310.

The X-ray detector 300 may further include a terminal 410 to which the coupling module 200 is connected. The terminal 410 may be provided in the X-ray detector 300 with which the coupling module 200 can be coupled. More specifically, the terminal 410 may be formed in one side of the side frame 390.

The X-ray detector 300 may further include a cap 420 which is configured to prevent foreign materials from entering the terminal 410 with which the coupling module 200 is coupled.

The top frame 360 may extend in the outward direction of the X-ray detector 300. More specifically, the top frame 360 may extend in the outward direction of the X-ray detector 300 such that at least one edge of the top frame 360 can rest on a top frame resting part 393 (see FIG. 18) formed in the side frame 390. Further, the top frame 360 may have a bent shape so that at least one edge of the top frame 360 can rest on the top frame resting part 393.

In another aspect, the top frame 360 may include a first area 361 and a second area 362 bent from the first area 361. The second area 362 may rest on the top frame resting part 393 formed in the side frame 390.

The X-ray detector 300 may further include an active area 700. In particular, the top frame 390 may further include the active area 700.

The size or location of the active area 700 may depend on the size or location of the sensing panel 330. More specifically, the fact that the location of the active area 700 changes means that the location of the sensing panel 330 accommodated in the accommodation space of the X-ray detector 300 changes. Further, the fact that the size of the active area 700 increases means that the size of the sensing panel 330 accommodated in the accommodation space of the X-ray detector 300 increases. In particular, the active area 700 may be formed on the top frame 360 to correspond to the sensing panel 330. More specifically, the active area 700 may be formed on the first area 361 of the top frame 360.

The active area 700 may be biased on the X-ray detector 300. In particular, the active area 700 may be formed on the first area 360 of the top frame 360 so as to be biased from the center of the first area 361 of the top frame 360. The fact that the active area 700 is formed in the center of the first area 361 means that the active area 700 is formed on the first area 361 of the top frame 360 so as to be spaced by the same distance from all the edges of the first area 361 of the top frame 360 in the inward direction of the X-ray detector 300. However, there is a case in which it is difficult to accurately position an object on the active area 700 formed in the center of the X-ray detector 300. For example, when an object to be scanned is an animal, it is difficult to position the object on the active area 700 formed in the center of the X-ray detector 300. If an object deviates from the active area 700 of the X-ray detector 300, it is difficult to accurately scan the object. In order to overcome the problem, the active area 700 may be biased on the X-ray detector 300. In particular, the active area 700 may be moved from the center of the X-ray detector 300 toward one edge of the X-ray detector 300.

A case in which the active area 700 is biased on the X-ray detector 300 will be described in detail, below. The first area 361 may include a first edge 361a which meets the second area 362, and a plurality of second edges 361b which define the first area 361 together with the first edge 361a. The active area 700 may be formed on the first area 361 so as to be biased from the center of the first area 361 toward the first edge 361a.

The active area 700 may include a first border area 710 which corresponds to the first edge 361a of the first area 361, and a plurality of second border areas 720 which form the active area 700 together with the first border area 710. If the active area 700 is formed on the first area 361 in such a way to be biased from the center of the first area 361, a distance d1 between the first edge 361a and the first border area 710 may be smaller than distances d2, d3, and d4 between the respective ones of plurality of second edges 361b and the corresponding ones of the plurality of second border areas 720.

Further, the active area 700 may expand in the outward direction of the X-ray detector 300. In particular, the active area 700 may expand in the outward direction of the first area 361 of the top frame 360. As such, by expanding the active area 700, it is possible to scan an object even when the object is located adjacent to one edge of the first area 361, as well as when the object is located in the center of the first area 361.

Figure 15:
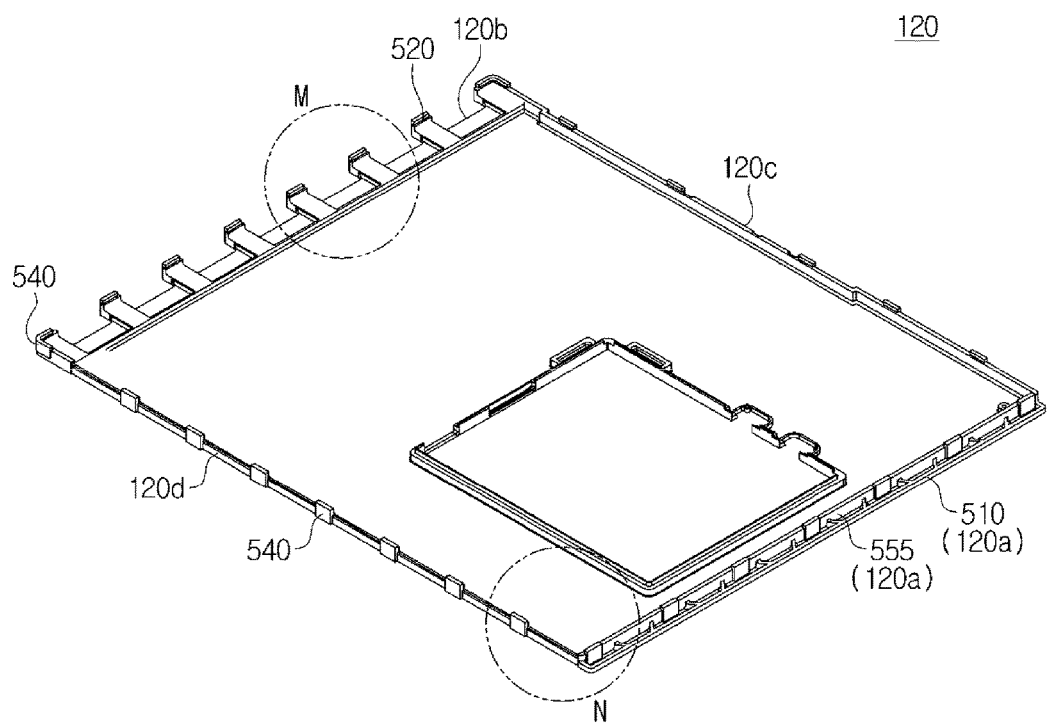
FIG. 15 is a bottom perspective view of a middle block of an X-ray imaging apparatus, according to an exemplary embodiment.
Figure 16A:
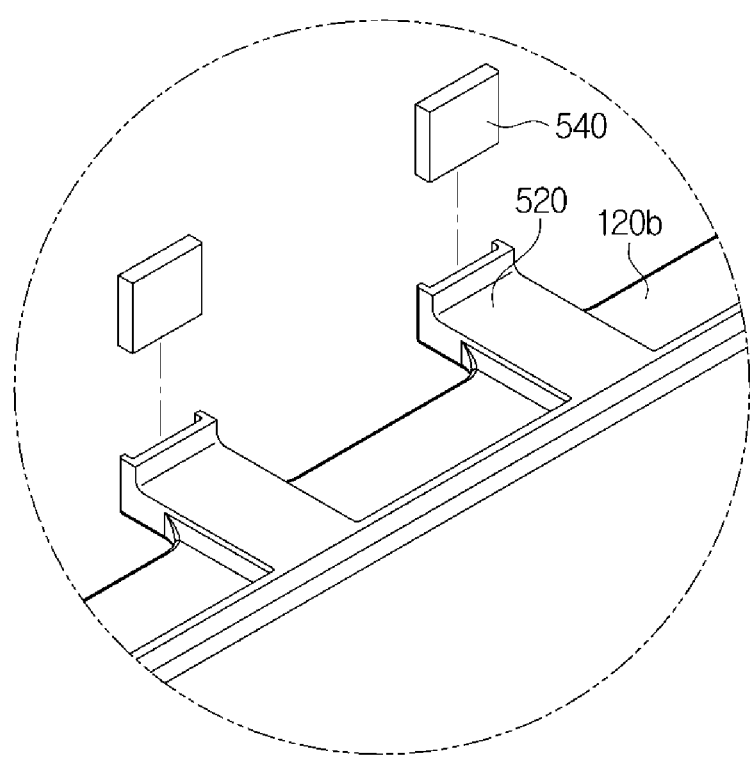
FIG. 16A is an enlarged view of an area M of FIG. 15, showing a coupling relationship between a middle block and a buffer member.
Figure 16B:
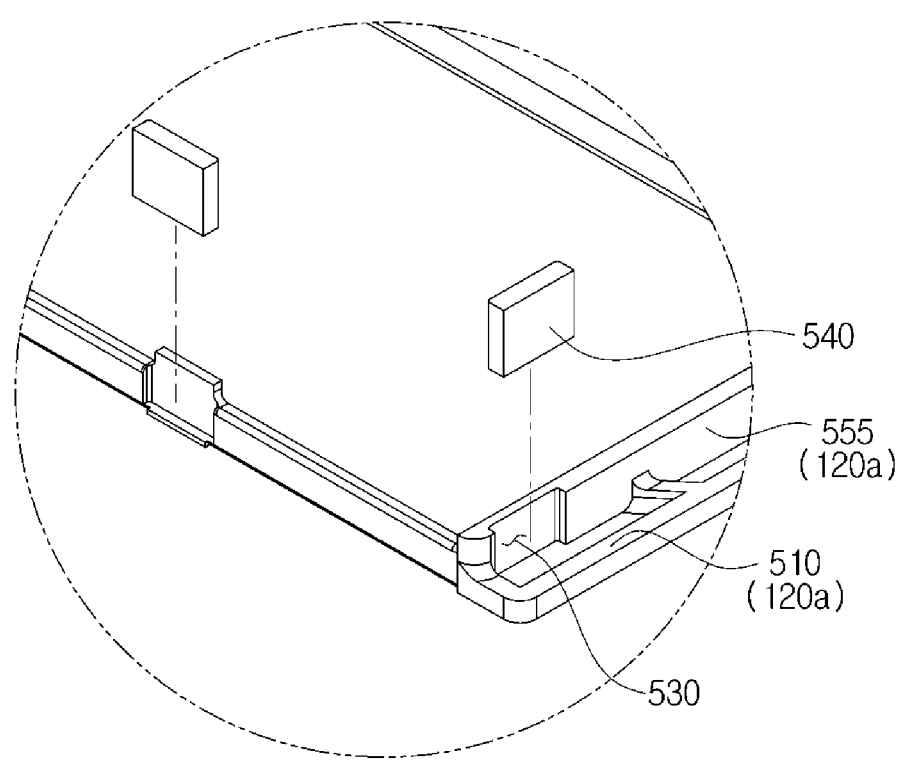
FIG. 16B is an enlarged view of an area N of FIG. 15, showing a coupling relationship between a middle block and a buffer member.
Figure 17:
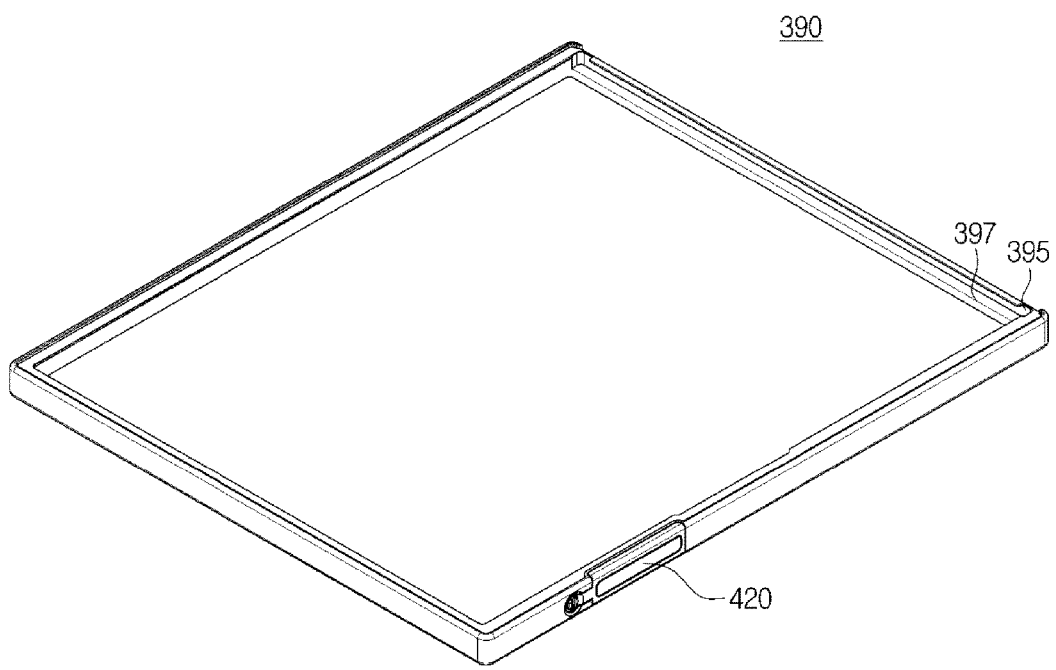
FIG. 17 is a perspective view of a side frame of an X-ray imaging apparatus, according to an exemplary embodiment.
Figure 18:
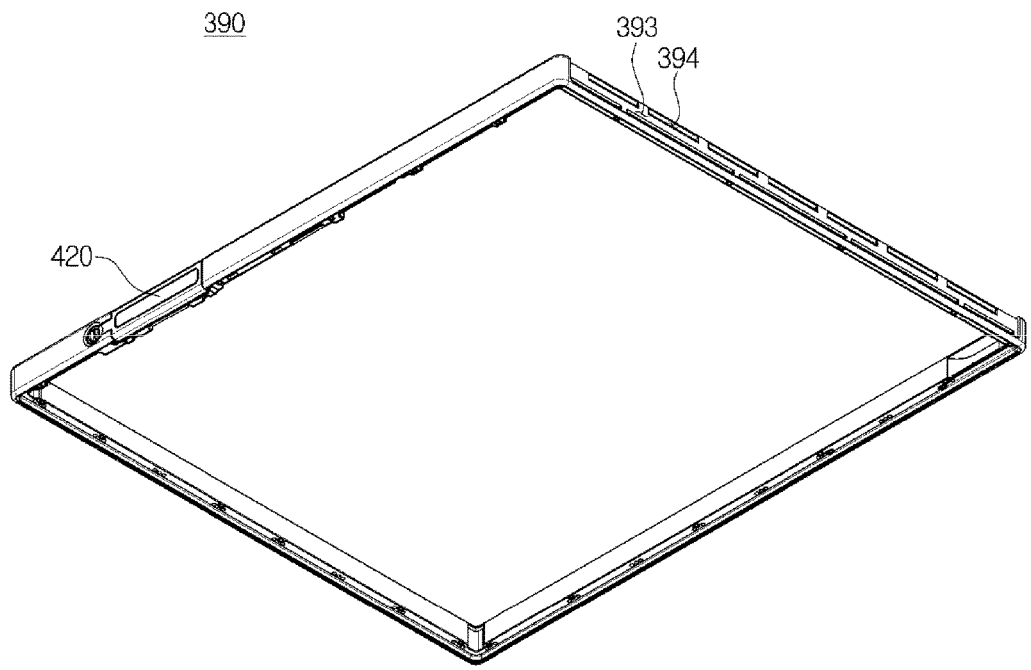
FIG. 18 is a bottom perspective view of a side frame of an X-ray imaging apparatus, according to an exemplary embodiment.
Figure 19:
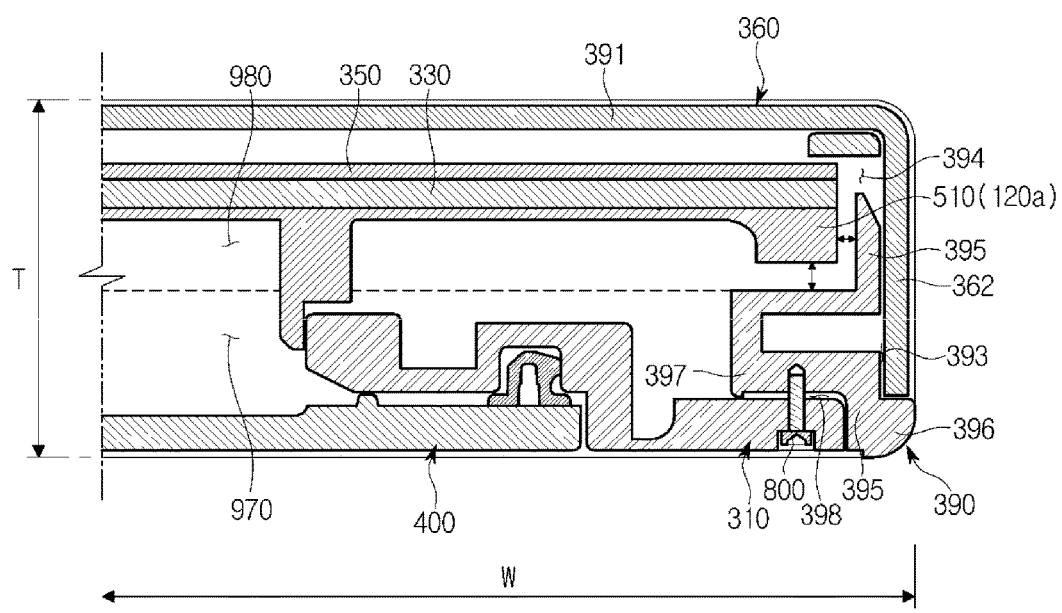
FIG. 19 is a cross-sectional view of an X-ray imaging apparatus according to an exemplary embodiment, cut along a line A-A' of FIG. 13, showing a first structure of a middle block and a side frame.

FIG. 15 is a bottom perspective view of the middle block 120 of the X-ray imaging apparatus 1 according to an exemplary embodiment, FIG. 16A is an enlarged view of an area M of FIG. 15, showing a coupling relationship between the middle block 120 and a buffer member, FIG. 16B is an enlarged view of an area N of FIG. 15, showing a coupling relationship between the middle block 120 and a buffer member, FIG. 17 is a perspective view of the side frame 390 of the X-ray imaging apparatus 1 according to an exemplary embodiment, FIG. 18 is a bottom perspective view of the side frame 390 of the X-ray imaging apparatus 1 according to an exemplary embodiment, and FIG. 19 is a cross-sectional view of the X-ray imaging apparatus 1 according to an exemplary embodiment, cut along a line A-A' of FIG. 13, showing a first structure of the middle block 120 and the side frame 390. FIG. 19 is a cross-sectional view to which the shapes of the top frame 360, the middle block 120, the side frame 390, the bottom frame 31, and the battery cover 400 shown in FIGS. 13 to 18 are reflected.

The sensing panel 330 may be accommodated in the accommodation space of the X-ray detector 300 such that the sensing panel 330 is biased. In particular, the sensing panel 330 may be biased from the center of the first area 361 toward one edge of the first area 361. Since the sensing panel 330 is supported by the middle block 120, biasing the sensing panel 330 in the accommodation space of the X-ray detector 300 may involve changing the structure of the middle block 120. Hereinbelow, the structure of the middle block 120 will be described in detail.

As shown in FIGS. 15 to 19, the middle block 120 may include a plurality of edges. The plurality of edges may include a first edge 120a, a second edge 120b, a third edge 120c, and a fourth edge 120d. The first edge 120a may be opposite to the second edge 120b, and the third edge 120c may be opposite to the fourth edge 120d. The middle block 120 may further include a coupling part 510. The coupling part 510 may protrude in an outward direction of the middle block 120. The coupling part 510 may be formed in one side edge of the middle block 120. More specifically, the coupling part 510 may be formed in the first edge 120a, and protrude in the outward direction of the middle block 120.

The first edge 120a may have a step. More specifically, the first edge 120a may include a first part 510 which extends toward the side frame 390, and a second part 555 which extends toward the bottom frame 310. The first part 510 may protrude in the outward direction of the middle block 120 so as to form a step in the first edge 120a. The coupling part 510 may be formed in the first part 510. In the current exemplary embodiment, since the first part 510 corresponds to the coupling part 510, the first part 510 and the coupling part 510 will be indicated by the same reference number "510". In the second part 555, a buffer member resting groove 530 may be formed.

The middle block 120 may further include a support part 520. The support part 520 may protrude in the outward direction of the middle block 120 so as to face an inner wall of the side frame 390. The support part 520 may be formed in one side edge of the middle block 120. More specifically, the support part 520 may be formed in the second edge 120b, and protrude in the outward direction of the middle block 120. The support part 520 may function to support the inner wall of the side frame 390 so that the middle block 120 can be fixed at the side frame 390. In the support part 520, a buffer member resting groove 530 may be formed.

The side frame 390 may include the top frame resting part 393 which is formed in an outer surface that faces the outside of the X-ray detector 300 and on which the second area 362 of the top frame 360 rests. The top frame resting part 393 may be formed in the outer surface of the side frame 390, and have a recessed shape that is recessed in an inward direction of the side frame 390.

The side frame 390 may further include a body 395. The body 395 may form one surface of the top frame resting part 393. Further, the body 395 may be positioned behind the second area 362 which rests on the top frame resting part 393, with respect to the inward direction of the X-ray detector 300.

The body 395 may extend in the thickness direction T of the X-ray detector 300 so as to be adjacent to the inner surface of the first area 361 of the top frame 360.

The body 395 may extend in the thickness direction T of the X-ray detector 300 so as to face at least one part of the inner surface of the second area 362 which rests on the top frame resting part 393.

The side frame 390 may include an outer protrusion part 396 which forms another surface of the top frame resting part 393, and protrudes from the body 395 in the outward direction of the X-ray detector 300. The second area 362 which rests on the top frame resting part 393 may be supported on the outer protrusion part 396.

The side frame 390 may further include an inner protrusion part 397 that protrudes from the body 395 in the inward direction of the X-ray detector 300.

The middle block 120 may be spaced from the side frame 390 in order to prevent an external impact that is applied on the side frame 390 from being transferred to the sensing panel 330.

More specifically, one edge of the middle block 120 may be located between the inner protrusion part 397 and the first area 361, as seen in the thickness direction T of the X-ray detector 300, such that the edge of the middle block 120 is spaced from the inner protrusion part 397.

Further, the middle block 120 may be spaced from the body 395.

The side frame 390 may further include a plurality of openings 394. The plurality of openings 394 may be formed in the body 395 which forms one surface of the top frame resting part 393. One edge of the top frame 360 may be fixed on the top frame resting part 393 by an adhesive material. The edge of the top frame 360 may be bent to be fixed on the top frame resting part 393. More specifically, the second area 362 of the top frame 360 may be fixed on the top frame resting part 393 by an adhesive material which passes through at least one from among the plurality of openings 394 from the accommodation space in the outward direction of the X-ray detector 300.

The side frame 390 may further include a bottom frame resting part 398. The bottom frame resting part 398 may be formed by one surface 397a of the inner protrusion part 397 and an inner surface 395a of the body 395 which faces the inside of the X-ray detector 300. One edge of the bottom frame 310 may rest on the bottom frame resting part 398.

The bottom frame 310 may be fixed at the side frame 390 by a fixing member 800 that penetrates through the bottom frame 310 in the thickness direction T of the X-ray detector 300. More specifically, the bottom frame 310 may be fixed at the inner protrusion part 397 of the side frame 390 by the fixing member 800 that penetrates through the bottom frame 310 in the thickness direction T of the X-ray detector 300. The fixing member 800 may be a screw, for example. The bottom frame 310 may be fixed at the side frame 390 by an adhesive material, as well as by the fixing member 800.

The X-ray imaging apparatus 1 may further include a buffer member 540. The buffer member 540 may be disposed between the side frame 390 and the middle block 120 in order to absorb an external impact. The buffer member 540 may be disposed along the edges of the middle block 120 so as to face the inner surfaces of the side frame 390. The buffer member 540 may be coupled with the middle block 120. More specifically, the buffer member 540 may be coupled with the buffer member resting groove 530. The buffer member resting groove 530 may be formed in the first edge 120a, the second edge 120b, the third edge 120c, and the fourth edge 120d of the middle block 120. More specifically, the buffer member resting groove 530 may be formed in the second part 555 of the first edge 120a. In addition, the buffer member resting groove 530 may be formed in the support part 520 formed in the second edge 120b. Further, the buffer member resting groove 530 may be formed in the third and fourth edges 120c and 120d. The buffer member 540 may also function to seal gaps between the middle block 120 and the side frame 390.

The middle block 120 may slide so that the coupling part 510 of the middle block 120 is located above the inner protrusion part 397 of the side frame 390 in the thickness direction T of the X-ray detector 300. If the middle block 120 slides so that the coupling part 510 of the middle block 120 is located above the inner protrusion part 397, the support part 520 of the middle block 120 may be indirectly supported on one inner surface of the side frame 390. In another aspect, a buffer member 540 may be disposed between the support part 520 of the middle block 120 and one inner wall of the side frame 390.

Figure 20:
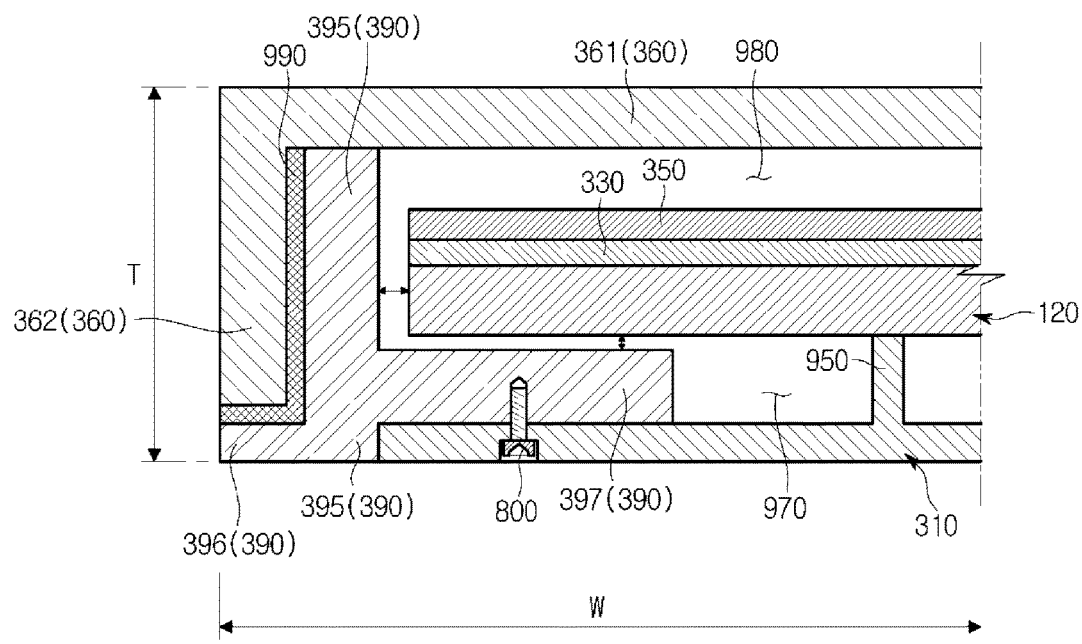
FIG. 20 is a cross-sectional view of an X-ray imaging apparatus according to an exemplary embodiment, cut along a line A-A' of FIG. 13, briefly showing a second structure of a middle block and a side frame.

Although not shown in FIG. 19, the middle block 120 may be supported on the bottom frame 310 by a support rib 950, which is shown in FIG. 20. The support rib 950 may extend from the bottom frame 310 toward the middle block 120 in the thickness direction T of the X-ray detector 300. In this case, the support rib 950 may be integrated into the bottom frame 310. Further, the support rib 950 may extend from the middle block 120 toward the bottom frame 310 in the thickness direction T of the X-ray detector 300. In this case, the support rib 950 may be integrated into the middle block 120. However, the support rib 950 may be separated from the bottom frame 310 or the middle block 120.

As shown in FIG. 19, the accommodation space may include a first accommodation space (also referred to herein as a "first accommodation subspace") 970 and a second accommodation space (also referred to herein as a "second accommodation subspace") 980. The second accommodation space 980 may be formed adjacent to the first area 361 in the thickness direction T of the X-ray detector 300. In this aspect, the second accommodation space 980 may be formed above the first accommodation space 970, as seen in the thickness direction T of the X-ray detector 300.

The second accommodation space 980 may have a greater width than the first accommodation space 970, as seen in the width direction W of the X-ray detector 300. The sensing panel 330 may expand in the outward direction of the X-ray detector 300, and be disposed in the second accommodation space 980. The active area 700 may expand in the outward direction of the first area 361 so as to correspond to the sensing panel 330.

The middle block 120 may be disposed in the second accommodation space 980 in order to support the sensing panel 330.

One edge of the middle block 120 may be located adjacent to the inner surface of the body 395, as seen in the width direction W of the X-ray detector 300.

FIG. 20 is a cross-sectional view of the X-ray imaging apparatus 1 according to an exemplary embodiment, cut along a line A-A' of FIG. 13, briefly showing a second structure of the middle block 120 and the side frame 390. Hereinafter, the same descriptions as those about the first structure of the middle block 120 and the side frame 390 will be omitted. Further, the same components as those described above with reference to FIGS. 1 to 19 will be allocated the same reference numbers.

As shown in FIG. 20, the sensing panel 330 may expand in the outward direction of the X-ray detector 300, and disposed in the second accommodation space 980, and the active area 700 may expand in the outward direction of the first area 361 so as to correspond to the sensing panel 330. Further, the middle block 120 may be disposed in the second accommodation space 980 in order to support the sensing panel 330.

The second area 362 may be fixed on the top frame resting part 393 by an adhesive material located between the second area 362 and the top frame resting part 393. The plurality of openings 394 formed in the body 395 may be omitted.

The middle block 120 may be supported on the bottom frame 310 by the support rib 950.

Figure 21:
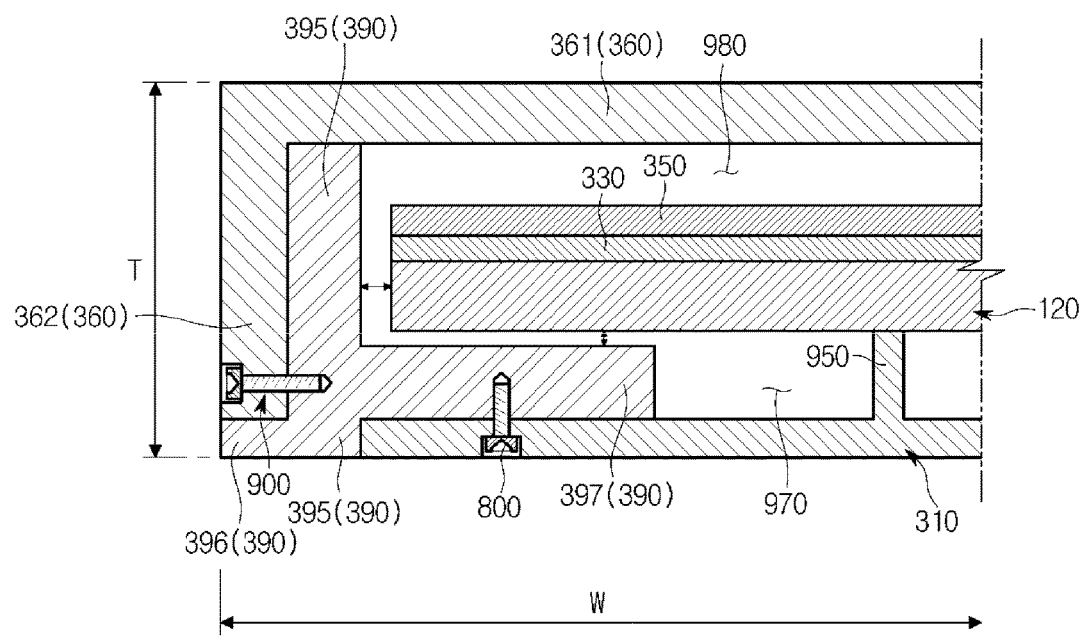
FIG. 21 is a cross-sectional view of an X-ray imaging apparatus according to an exemplary embodiment, cut along a line A-A' of FIG. 13, briefly showing a third structure of a middle block and a side frame.

FIG. 21 is a cross-sectional view of the X-ray imaging apparatus 1 according to an exemplary embodiment, cut along a line A-A' of FIG. 13, briefly showing a third structure of the middle block 120 and the side frame 390. Hereinafter, the same descriptions as those about the first structure of the middle block 120 and the side frame 390 will be omitted. Further, the same components as those described above with reference to FIGS. 1 to 19 will be allocated the same reference numbers.

As shown in FIG. 21, the second area 362, which rests on the top frame resting part 393, may be fixed at the body 395 by a coupling member 900 that penetrates through the second area 362 in the inward direction of the X-ray detector 300. The coupling member 900 may be a screw, for example.

Figure 22:
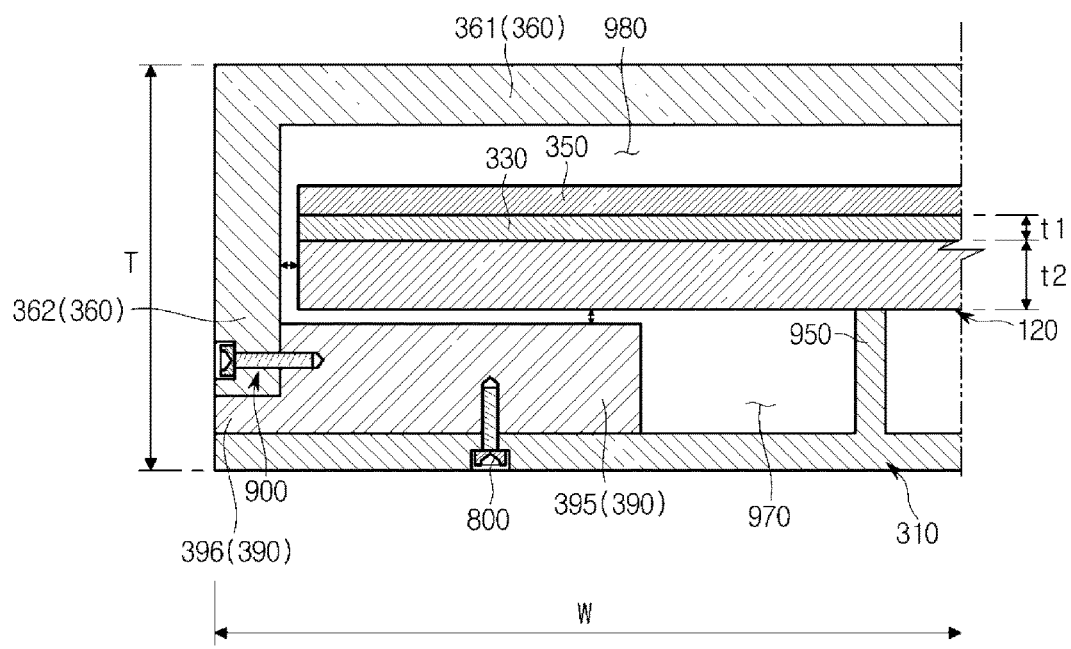
FIG. 22 is a cross-sectional view of an X-ray imaging apparatus according to an exemplary embodiment, cut along a line A-A' of FIG. 13, briefly showing a fourth structure of a middle block and a side frame.

FIG. 22 is a cross-sectional view of the X-ray imaging apparatus 1 according to an exemplary embodiment, cut along a line A-A' of FIG. 13, briefly showing a fourth structure of the middle block 120 and the side frame 390. Hereinafter, the same descriptions as those about the first structure of the middle block 120 and the side frame 390 will be omitted. Further, the same components as those described above with reference to FIGS. 1 to 19 will be allocated the same reference numbers.

As shown in FIG. 22, the side frame 390 may include the body 395 which extends in the inward direction of the X-ray detector 300. The body 395 may form one surface of the top frame resting part 393. In addition, the body 395 may be disposed behind the second area 362 which rests on the top frame resting part 393, with respect to the inward direction of the X-ray detector 300.

The body 395 may extend in the thickness direction T of the X-ray detector 300 so as to face a part of the inner surface of the second area 362 which rests on the top frame resting part 393. In another aspect, the body 395 may extend in the thickness direction T of the X-ray detector 300, and be spaced from the inner surface of the first area 361 by a distance that is equal to or greater than a sum of a first thickness t1 that is the thickness of the sensing panel 330 and a second thickness t2 that is the thickness of the middle block 120, so that one edge of the sensing panel 330 and one edge of the middle block 120 are disposed between the inner surface of the first area 361 and one surface of the body 395 that is opposite to the first area 361.

At least one of one edge of the sensing panel 330 and one edge of the middle block 120 may be located behind the second area 362, with respect to the inward direction of the X-ray detector 300, so as to directly face the inner surface of the second area 362 while being adjacent to the inner surface of the second area 362.

The side frame 390 may further include an outer protrusion part 396 which forms another surface of the top frame resting part 393 and protrudes from the body 395 in the outward direction of the X-ray detector 300. The second area 362, which rests on the top frame resting part 393, may be supported on the outer protrusion part 396.

The second area 362, which rests on the top frame resting part 393, may be fixed at the body 395 by the coupling member 900 that penetrates through the second area 362 in the inward direction of the X-ray detector 300. The coupling member 900 may be a screw.

Figure 23:
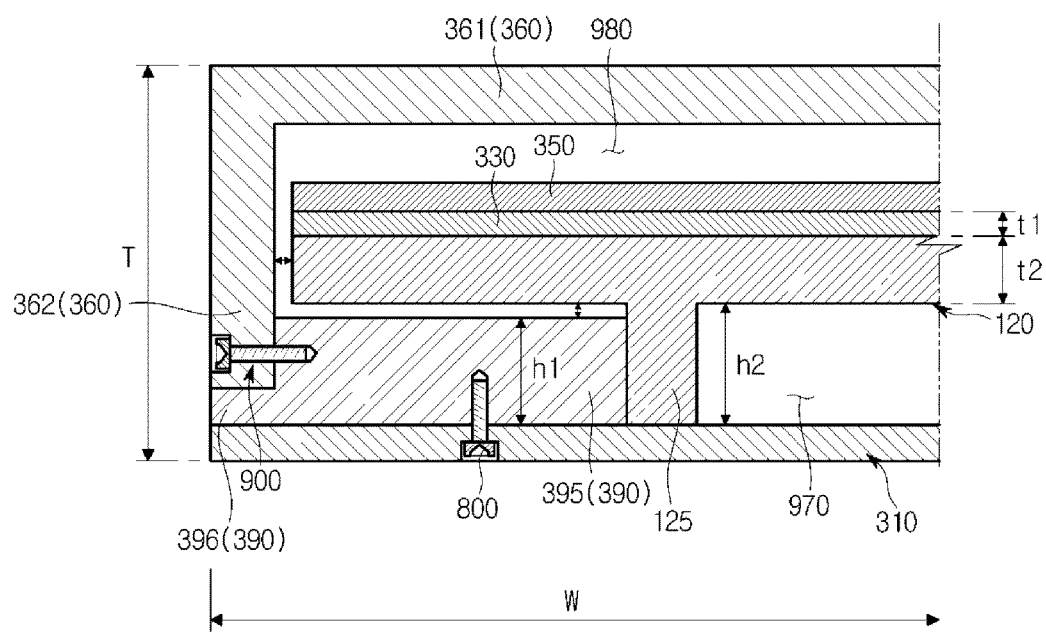
FIG. 23 is a cross-sectional view of an X-ray imaging apparatus according to an exemplary embodiment, cut along a line A-A' of FIG. 13, briefly showing a fifth structure of a middle block and a side frame.

FIG. 23 is a cross-sectional view of the X-ray imaging apparatus 1 according to an exemplary embodiment, cut along a line A-A' of FIG. 13, briefly showing a fifth structure of the middle block 120 and the side frame 390. Hereinafter, the same descriptions as those about the first structure of the middle block 120 and the side frame 390 will be omitted. Further, the same components as those described above with reference to FIGS. 1 to 19 will be allocated the same reference numbers.

As shown in FIG. 23, the side frame 390 may include the body 395 which extends in the inward direction of the X-ray detector 300. The body 395 may form one surface of the top frame resting part 393. In addition, the body 395 may be disposed behind the second area 362 which rests on the top frame resting part 393, with respect to the inward direction of the X-ray detector 300.

The body 395 may extend in the thickness direction T of the X-ray detector 300 so as to face a part of the inner surface of the second area 362 which rests on the top frame resting part 393. In another aspect, the body 395 may extend in the thickness direction T of the X-ray detector 300, and be spaced from the inner surface of the first area 361 by a distance that is equal to or greater than a sum of a first thickness t1 that is the thickness of the sensing panel 330 and a second thickness t2 that is the thickness of the middle block 120, so that one edge of the sensing panel 330 and one edge of the middle block 120 are disposed between the inner surface of the first area 361 and one surface of the body 395 that is opposite to the first area 361.

At least one of one edge of the sensing panel 330 and one edge of the middle block 120 may be located behind the second area 362, with respect to the inward direction of the X-ray detector 300, so as to directly face the inner surface of the second area 362 while being adjacent to the inner surface of the second area 362.

The side frame 390 may further include the outer protrusion part 396 which forms another surface of the top frame resting part 393 and protrudes from the body 395 in the outward direction of the X-ray detector 300. The second area 362, which rests on the top frame resting part 393, may be supported on the outer protrusion part 396.

The second area 362 which rests on the top frame resting part 393 may be fixed at the body 395 by the coupling member 900 that penetrates through the second area 362 in the inward direction of the X-ray detector 300. The coupling member 900 may be a screw.

The middle block 120 may include a rib 125 which protrudes in the thickness direction T of the X-ray detector 300 so that the middle block 120 is spaced from the active area 700.

The rib 125 may limit movement of the middle block 120 by interfering with one edge of the body 395 which extends in the inward direction of the X-ray detector 300 so that one edge of the middle block 120 is spaced by a predetermined distance from the inner surface of the second area 362. Further, the middle block 120 may be supported on the bottom frame 310 by the rib 125.

The rib 125 may have a height h2 that is greater than a height h1 of the body 395 in the thickness direction T of the X-ray detector 300. This is aimed to separate the middle block 120 from the body 395 in the thickness direction T of the X-ray detector 300.

The bottom frame 310 may be fixed on one surface of the side frame 390. More specifically, the bottom frame 310 may be fixed on the lower surface of the side frame 390 by the fixing member 800.

Figure 24:
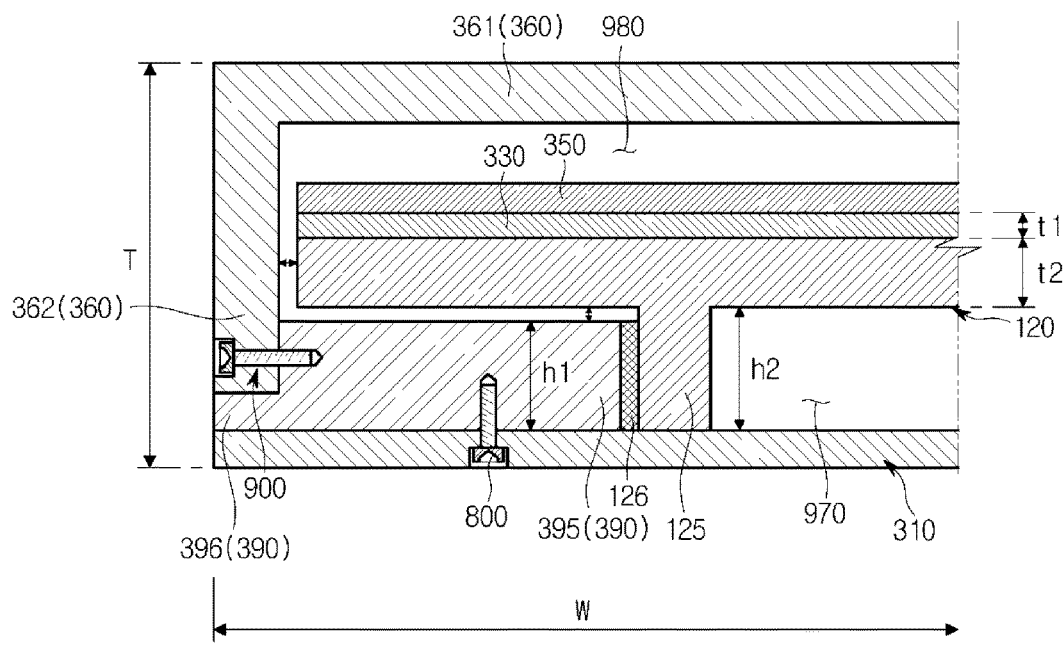
FIG. 24 is a cross-sectional view of an X-ray imaging apparatus according to an exemplary embodiment, cut along a line A-A' of FIG. 13, briefly showing a sixth structure of a middle block and a side frame.

FIG. 24 is a cross-sectional view of the X-ray imaging apparatus 1 according to an exemplary embodiment, cut along a line A-A' of FIG. 13, briefly showing a sixth structure of the middle block 120 and the side frame 390. Hereinafter, the same descriptions as those about the first structure of the middle block 120 and the side frame 390 will be omitted. Further, the same components as those described above with reference to FIGS. 1 to 19 will be allocated the same reference numbers.

As shown in FIG. 24, the side frame 390 may include the body 395 which extends in the inward direction of the X-ray detector 300. The body 395 may form one surface of the top frame resting part 393. Further, the body 395 may be disposed behind the second area 362 which rests on the top frame resting part 393, with respect to the inward direction of the X-ray detector 300.

The body 395 may extend in the thickness direction T of the X-ray detector 300 so as to face a part of the inner surface of the second area 362 which rests on the top frame resting part 393. In another aspect, the body 395 may extend in the thickness direction T of the X-ray detector 300, and be spaced from the inner surface of the first area 361 by a distance that is equal to or greater than a sum of a first thickness t1 that is the thickness of the sensing panel 330 and a second thickness t2 that is the thickness of the middle block 120, so that one edge of the sensing panel 330 and one edge of the middle block 120 are disposed between the inner surface of the first area 361 and one surface of the body that is opposite to the first area 361.

At least one of one edge of the sensing panel 330 and one edge of the middle block 120 may be located behind the second area 362, with respect to the inward direction of the X-ray detector 300, so as to directly face the inner surface of the second area 362 while being adjacent to the inner surface of the second area 362.

The side frame 390 may further include the outer protrusion part 396, which forms another surface of the top frame resting part 393 and protrudes from the body 395 in the outward direction of the X-ray detector 300. The second area 362, which rests on the top frame resting part 393, may be supported on the outer protrusion part 396.

The second area 362 which rests on the top frame resting part 393 may be fixed at the body 395 by the coupling member 900 that penetrates through the second area 362 in the inward direction of the X-ray detector 300. The coupling member 900 may be a screw.

The middle block 120 may include the rib 125 which protrudes in the thickness direction T of the X-ray detector 300 so that the middle block 120 is spaced from the active area 700.

The rib 125 may have a height h2 that is greater than a height h1 of the body 395 in the thickness direction T of the X-ray detector 300. This is aimed to separate the middle block 120 from the body 395 in the thickness direction T of the X-ray detector 300.

The bottom frame 310 may be fixed on one surface of the side frame 390. More specifically, the bottom frame 310 may be fixed on the lower surface of the side frame 390 by the fixing member 800.

The buffer member 126 may be disposed between the rib 125 and one edge of the body 395 which faces the inside of the X-ray detector 300. The buffer member 126 may function to prevent the body 395 from directly contacting the rib 125 to thereby prevent an external impact that is applied on the side frame 390 from being easily transferred to the sensing panel 330.

Figure 25:
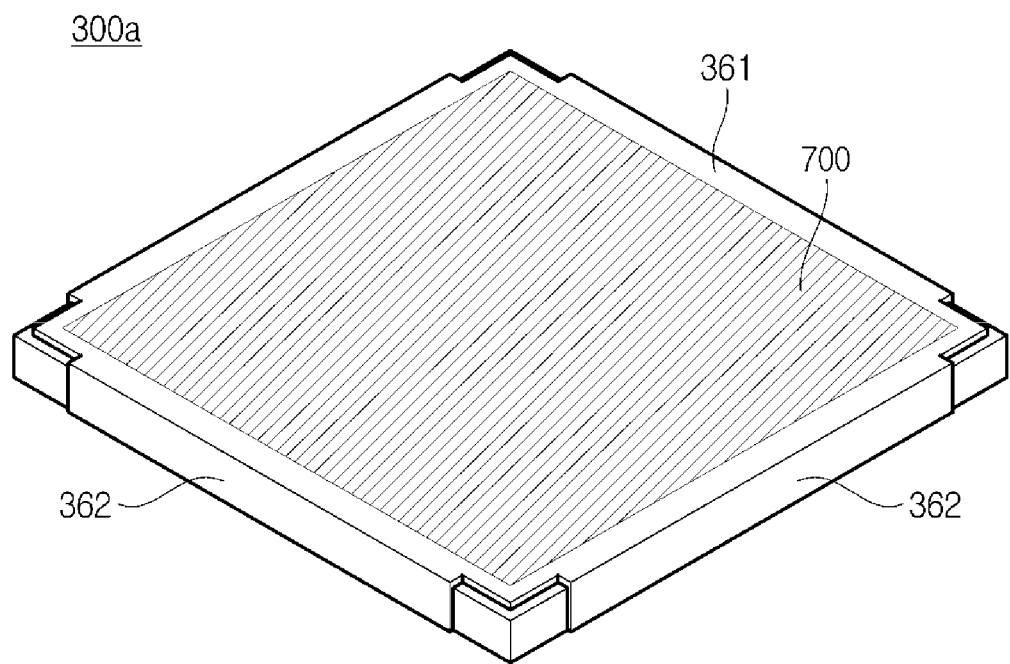
FIG. 25 is a perspective view of an X-ray detector of an X-ray imaging apparatus, according to another exemplary embodiment.

FIG. 25 is a perspective view of an X-ray detector of an X-ray imaging apparatus, according to another exemplary embodiment. Hereinafter, the same descriptions as those described above with reference to FIGS. 13 to 19 will be omitted. Reference numbers not denoted in FIG. 25 will be understood by referring to FIGS. 13 to 19.

As shown in FIG. 25, an X-ray detector 300a may include a first area 361, a plurality of second areas 362 which are bent from the first area 361, and an active area 700 which is formed on the first area 361 and which expands in the outward direction of the first area 361. The plurality of second areas 362 may be respectively positioned on a plurality of top frame resting parts 393 formed in the outer surfaces of the side frame 390.

The X-ray detector 300 described above may be applied to an outdoor detector, as well as an indoor detector.

As described above, by disposing the sensing panel in the second accommodation space such that the sensing panel expands in the outward direction of the X-ray detector, it is possible to expand the active area that corresponds to the sensing panel in the outward direction of the X-ray detector.

By disposing the sensing panel in the accommodation area such that the sensing panel is adjacent to the inner surface of the body of the side frame or the inner surface of the second area of the top frame, it is possible to bias the active area from the center of the first area of the top frame.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. An X-ray detector configured to detect X-rays irradiated from an X-ray source, the X-ray detector comprising:
   a top frame that includes a first area having an active area which is biased from a center of the first area and a second area which is bent from the first area;
   a side frame that includes a top frame resting part which is formed in an outer surface which faces an outside of the X-ray detector and on which the second area rests, the side frame being coupled with the top frame to form an accommodation space, the side frame including a first side edge and a second side edge opposite to the first side edge; and
   a sensor panel disposed in the accommodation space and configured to convert the detected X-rays into an electrical signal, a location of the sensor panel being biased from the center of the first area to correspond to the active area, and
   wherein the sensor panel is biased, in a width direction of the X-ray detector, towards the first side edge of the side frame so that a distance between the first side edge of the side frame and one side of the sensor panel which faces the first side edge of the side frame is smaller than a distance between the second side edge of the side frame and the other side of the sensor panel which faces the second side edge of the side frame.

2. The X-ray detector according to claim 1, wherein the first area comprises:
   a first edge which meets the second area; and
   a plurality of second edges which define the first area together with the first edge,
   wherein the active area is formed in the first area so as to be biased toward the first edge from the center of the first area.

3. The X-ray detector according to claim 2, wherein the active area comprises:
   a first border area that corresponds to the first edge; and
   a plurality of second border areas which constitute the active area together with the first border area,
   wherein a distance between the first edge and the first border area is smaller than each of respective distances between each of the plurality of second edges and each of the plurality of second border areas.

4. The X-ray detector according to claim 1, wherein the side frame comprises:
   a body which forms a first surface of the top frame resting part, and which is disposed behind the second area with respect to an inward direction of the X-ray detector; and
   an outer protrusion part which forms a second surface of the top frame resting part, and which protrudes from the body in an outward direction of the X-ray detector.

5. The X-ray detector according to claim 4, wherein the body extends in a thickness direction of the X-ray detector so as to be adjacent to an inner surface of the first area.

6. The X-ray detector according to claim 5, wherein the side frame further comprises an inner protrusion part which protrudes from the body in the inward direction of the X-ray detector.

7. The X-ray detector according to claim 6, further comprising a middle block disposed in the accommodation space, and configured to support the sensor panel,
   wherein a first edge of the middle block is located between the inner protrusion part and the first area, with respect to the thickness direction of the X-ray detector, such that the first edge of the middle block is spaced from the inner protrusion part.

8. The X-ray detector according to claim 6, further comprising a middle block disposed in the accommodation space, and configured to support the sensor panel,
   wherein the middle block is spaced from the body in order to prevent an external impact that is applied on the side frame from being transferred to the sensor panel.

9. The X-ray detector according to claim 6, further comprising a bottom frame which forms an outer appearance of the X-ray detector together with the top frame and the side frame, wherein a first edge of the bottom frame rests on a bottom frame resting part formed by a first surface of the inner protrusion part and a first surface of the body which faces an inside of the X-ray detector.

10. The X-ray detector according to claim 9, wherein the bottom frame is fixed at the inner protrusion part by a fixing member that penetrates through the bottom frame in the thickness direction of the X-ray detector.

11. The X-ray detector according to claim 4, wherein the second area is fixed on the top frame resting part by an adhesive material located between the second area and the top frame resting part.

12. The X-ray detector according to claim 4, wherein a plurality of openings are formed in the body, and
wherein the second area is coupled with the top frame resting part by an adhesive material which passes through at least one from among the plurality of openings from the accommodation space in the outward direction of the X-ray detector.

13. The X-ray detector according to claim 4, wherein the second area is fixed at the body by a coupling member that penetrates through the second area in the inward direction of the X-ray detector.

14. The X-ray detector according to claim 4, wherein the body extends in the inward direction of the X-ray detector.

15. The X-ray detector according to claim 14, further comprising a middle block disposed in the accommodation space, and configured to support the sensor panel,
wherein the body extends in a thickness direction of the X-ray detector, and is spaced from an inner surface of the first area by a distance that is equal to or greater than a sum of a first thickness that is a thickness of the sensor panel and a second thickness that is a thickness of the middle block, so that a first edge of the sensor panel and a first edge of the middle block are disposed between the inner surface of the first area and a first surface of the body that is opposite to the first area.

16. The X-ray detector according to claim 15, wherein at least one from among the first edge of the sensor panel and the first edge of the middle block is located behind the second area, with respect to the inward direction of the X-ray detector, so as to directly face an inner surface of the second area while being adjacent to the inner surface of the second area.

17. The X-ray detector according to claim 16, wherein the middle block comprises a rib that protrudes in the thickness direction of the X-ray detector so that the middle block is spaced from the active area, and
wherein the rib limits a movement of the middle block by interfering with a first edge of the body which extends in the inward direction of the X-ray detector so that a second edge of the middle block is spaced by a predetermined distance from the inner surface of the second area.

18. The X-ray detector according to claim 17, wherein a buffer member is disposed between the rib and the first edge of the body.

19. The X-ray detector according to claim 15, wherein the middle block comprises a rib that protrudes in the thickness direction of the X-ray detector so that the middle block is spaced from the active area, and
a height of the rib is greater than a height of the body in the thickness direction of the X-ray detector.

20. The X-ray detector according to claim 1, further comprising:
a circuit board that is disposed apart from the sensor panel in a thickness direction of the X-ray detector.

21. The X-ray detector according to claim 1, wherein a center of the sensor panel is biased towards the second area in the width direction of the X-ray detector that is perpendicular to a thickness direction of the X-ray detector.

* * * * *